(12) United States Patent
Morgan et al.

(10) Patent No.: US 10,143,724 B2
(45) Date of Patent: Dec. 4, 2018

(54) ANTI-SSX-2 T CELL RECEPTORS AND RELATED MATERIALS AND METHODS OF USE

(71) Applicant: The United States of America, as represented by the Secretary, Department of Health and Human Services, Washington, DC (US)

(72) Inventors: Richard A. Morgan, Columbia, MD (US); Nachimuthu Chinnasamy, North Potomac, MD (US); Steven A. Rosenberg, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 127 days.

(21) Appl. No.: 15/132,863

(22) Filed: Apr. 19, 2016

(65) Prior Publication Data

US 2016/0279196 A1  Sep. 29, 2016

Related U.S. Application Data

(62) Division of application No. 13/820,802, filed as application No. PCT/US2011/051537 on Sep. 14, 2011, now Pat. No. 9,345,748.

(60) Provisional application No. 61/384,931, filed on Sep. 21, 2010.

(51) Int. Cl.
| | |
|---|---|
| *A61K 38/17* | (2006.01) |
| *C07K 14/725* | (2006.01) |
| *A61K 31/706* | (2006.01) |
| *A61K 38/08* | (2006.01) |
| *A61K 38/10* | (2006.01) |
| *C07K 16/28* | (2006.01) |
| *A61K 39/395* | (2006.01) |
| *C07K 16/30* | (2006.01) |
| *G01N 33/574* | (2006.01) |

(52) U.S. Cl.
CPC ........ *A61K 38/1774* (2013.01); *A61K 31/706* (2013.01); *A61K 38/08* (2013.01); *A61K 38/10* (2013.01); *A61K 38/177* (2013.01); *A61K 39/39558* (2013.01); *C07K 14/7051* (2013.01); *C07K 16/2809* (2013.01); *C07K 16/30* (2013.01); *G01N 33/57492* (2013.01); *C07K 2319/00* (2013.01)

(58) Field of Classification Search
None
See application file for complete search history.

(56) References Cited

U.S. PATENT DOCUMENTS

| | | |
|---|---|---|
| 5,087,616 A | 2/1992 | Myers et al. |
| 5,225,539 A | 7/1993 | Winter |
| 5,449,752 A | 9/1995 | Fujii et al. |
| 5,545,806 A | 8/1996 | Lonberg et al. |
| 5,569,825 A | 10/1996 | Lonberg et al. |
| 5,585,089 A | 12/1996 | Queen et al. |
| 5,639,641 A | 6/1997 | Pedersen et al. |
| 5,693,761 A | 12/1997 | Queen et al. |
| 5,714,352 A | 2/1998 | Jakobovits |
| 6,265,150 B1 | 7/2001 | Terstappen et al. |
| 2002/0197266 A1 | 12/2002 | Debinski |
| 2004/0082012 A1 | 4/2004 | Busch et al. |
| 2004/0180354 A1 | 9/2004 | Simard et al. |
| 2006/0057673 A1 | 3/2006 | Liu et al. |
| 2006/0063913 A1 | 3/2006 | Liu et al. |
| 2006/0189001 A1 | 8/2006 | Valmori et al. |

FOREIGN PATENT DOCUMENTS

| | | | |
|---|---|---|---|
| CN | 101001868 A | 7/2007 | |
| EP | 0 239 400 B1 | 8/1994 | |
| GB | 2 188 638 A | 10/1987 | |
| JP | 2004-525354 A | 8/2004 | |
| WO | WO-2004097052 A2 * | 11/2004 | ........... C12Q 1/6886 |
| WO | WO 2005/010190 A1 | 2/2005 | |
| WO | WO-2007131092 A2 * | 11/2007 | ......... C07K 14/7051 |
| WO | WO-2008039694 A2 * | 4/2008 | ........... C12Q 1/6883 |
| WO | WO-2010088160 A1 * | 8/2010 | ........... C07K 14/705 |

OTHER PUBLICATIONS

Soluble, High Affinity T Cell Receptors as Cancer Therapeutics, Bent Jakobsen, as part of iSBTC 24th Annual Meeting Oct. 29-31, 2009, Washington, D.C., cover page + pp. 1-18. (Year: 2009).*
Ayyoub et al., "Distinct but overlapping T helper epitopes in the 37-58 region of SSX-2," *Clinical Immunology*, 114: 70-78 (2005).
Chinese Patent Office, First Office Action in Chinese Patent Application No. 2011800454920 (dated Jun. 16, 2014).
Ayyoub et al., "An immunodominant SSX-2—derived epitope recognized by CD4+ T cells in association with HLA-DR," *J. Clin. Invest.*, 113 (8), 1225-1233 (2004).
Ayyoub et al., "Proteasome-Assisted Identification of a SSX-2-Derived Epitope Recognized by Tumor-Reactive CTL Infiltrating Metastatic Melanoma," *J. Immunology*, 168 (4), 1717-1722 (2002).

(Continued)

*Primary Examiner* — Zachary S Skelding
(74) *Attorney, Agent, or Firm* — Leydig, Voit & Mayer

(57) ABSTRACT

The invention provides an isolated or purified T cell receptor (TCR) having antigenic specificity for synovial sarcoma X Breakpoint (SSX)-2. The invention further provides related polypeptides and proteins, as well as related nucleic acids, recombinant expression vectors, host cells, and populations of cells. Further provided by the invention are antibodies, or an antigen binding portion thereof, and pharmaceutical compositions relating to the TCRs of the invention. Methods of detecting the presence of cancer in a host and methods of treating or preventing cancer in a host are further provided by the invention.

23 Claims, 14 Drawing Sheets

Specification includes a Sequence Listing.

(56) References Cited

OTHER PUBLICATIONS

Ayyoub et al., "Tumor-reactive, SSX-2-specific CD8+ T Cells Are Selectively Expanded during Immune Responses to Antigen-expressing Tumors in Melanoma Patients," *Cancer Res.*, 63 (17), 5601-5606 (2003).
Bricard et al., "Naturally Acquired MAGE-A10- and SSX-2-Specific CD8+ T Cell Responses in Patients with Hepatocellular Carcinoma," *J. Immunol.*, 174, 1709-1716 (2005).
Caballero et al., "Cancer testis (CT) antigens: Potential targets for immunotherapy," *Cancer Sci.*, 100 (11), 2014-2021 (2009).
Chinnasamy et al., "Development of HLA-A2 restricted TCR against cancer testis antigen SSX-2 for adoptive immunotherapy of cancer," Abstract submitted to the International Society for Biological Therapy of Cancer (ISBTC) annual meeting, Oct. 2-4, 2010.
Chinnasamy et al., "Development of T Cell Receptor Targeting the HLA-A*0201 Restricted Epitope SSX2: 41-49 for Adoptive Immunotherapy of Cancer," Poster Session: Cancer—Immunotherapy I (4:40 pm-6:40 pm), May 19, 2011.
Choi et al., "Synthesis and assembly of a cholera toxin B subunit-rotavirus VP7 fusion protein in transgenic potato," *Mol. Biotechnol.*, 31 (3), 193-202 (2005).
"Evaluating subject Matter Eligibility Under 35 U.S.C. § 101," Mar. 19, 2014 update, pp. 1-93.
GenBank Accession No. ABO16436.1 (printed Sep. 23, 2008).
GenBank Accession No. ACF49241.1 (printed Jul. 26, 2008).
GenBank Accession No. ACF75415.1 (printed Aug. 2, 2008).
Genbank Accession No. A31326 (Jul. 23, 1999).
Genbank Accession No. CAB96920 (Jul. 8, 2000).
Genbank Accession No. NP_003138 XP_942599 (Mar. 14, 2009).
Gure et al., "The SSX Gene Family: Characterization of 9 Complete Genes," *Int. J. Cancer*, 101, 448-453 (2002).
Haskard et al., "The production of human monoclonal autoantibodies from patients with rheumatoid arthritis by the EBV-hybridoma technique," *J. Immunol. Methods*, 74 (2), 361-367 (1984).
He et al., "Identification of a common HLA-A*0201-restricted epitope among SSX family members by mimicking altered peptide ligands strategy," *Mol. Immunol.*, 45 (9), 2455-2464 (2008).
Hudecz, "Synthesis of peptide bioconjugates," *Methods Mol. Biol.*, 298, 209-223 (2005).

Huse et al., "Generation of a large combinatorial library of the immunoglobulin repertoire in phage lambda," *Science*, 246 (4935), 1275-1281 (1989).
International Preliminary Report on Patentability, Application No. PCT/US2011/051537, dated Mar. 26, 2013.
International Search Report, Application No. PCT/US2011/051537, dated Mar. 29, 2012.
Kirin et al., "Amino acid and peptide bioconjugates of copper(II) and zinc(II) complexes with a modified N,N-bis(2-picolyl)amine ligand," *Inorg Chem.*, 44 (15), 5405-5415 (2005).
Köhler et al., "Derivation of specific antibody-producing tissue culture and tumor lines by cell fusion," *Eur. J. Immunol.*, 6 (7), 511-519 (1976).
Li et al., "Directed evolution of human T-cell receptors with picomolar affinities by phage display," *Nat. Biotechnol.*, 23(3): 349-54 (2005).
The MEMORANDUM emorandum from Deputy Commissioner for Patent Examination Policy Andrew H. Hirshfeld, dated Mar. 4, 2014, 19 pages.
Pedersen et al., "Comparison of surface accessible residues in human and murine immunoglobulin Fv domains. Implication for humanization of murine antibodies," *J. Mol. Biol.*, 235 (3), 959-973 (1994).
Reiter et al., "Engineering interchain disulfide bonds into conserved framework regions of Fv fragments: improved biochemical characteristics of recombinant immunotoxins containing disulfide-stabilized Fv," *Protein Eng.*, 7 (5), 697-704 (1994).
Richman et al., "Display, engineering, and applications of antigen-specific T cell receptors," *BioEng.*, 24 (4), 361-373 (2007).
Roder et al., "The EBV-hybridoma technique," *Methods Enzymol.*, 121, 140-167 (1986).
Taylor et al., "SSX Cancer Testis Antigens are Expressed in Most Multiple Myeloma Patients: Co-Expression of SSX1, 2, 4, and 5 Correlates With Adverse Prognosis and High Frequencies of SSX-Positive PCs," *J. Immunother*, 28: 564-575 (2005).
Türeci et al., "Expression of SSX genes in human tumors," *Int. J. Cancer*, 77: 19-23 (1998).
Wadwa et al., "Receptor mediated glycotargeting," *J. Drug Target.*, 3 (2), 111-127 (1995).
Written Opinion of the International Searching Authority, Application No. PCT/US2011/051537, dated Mar. 21, 2013.

* cited by examiner

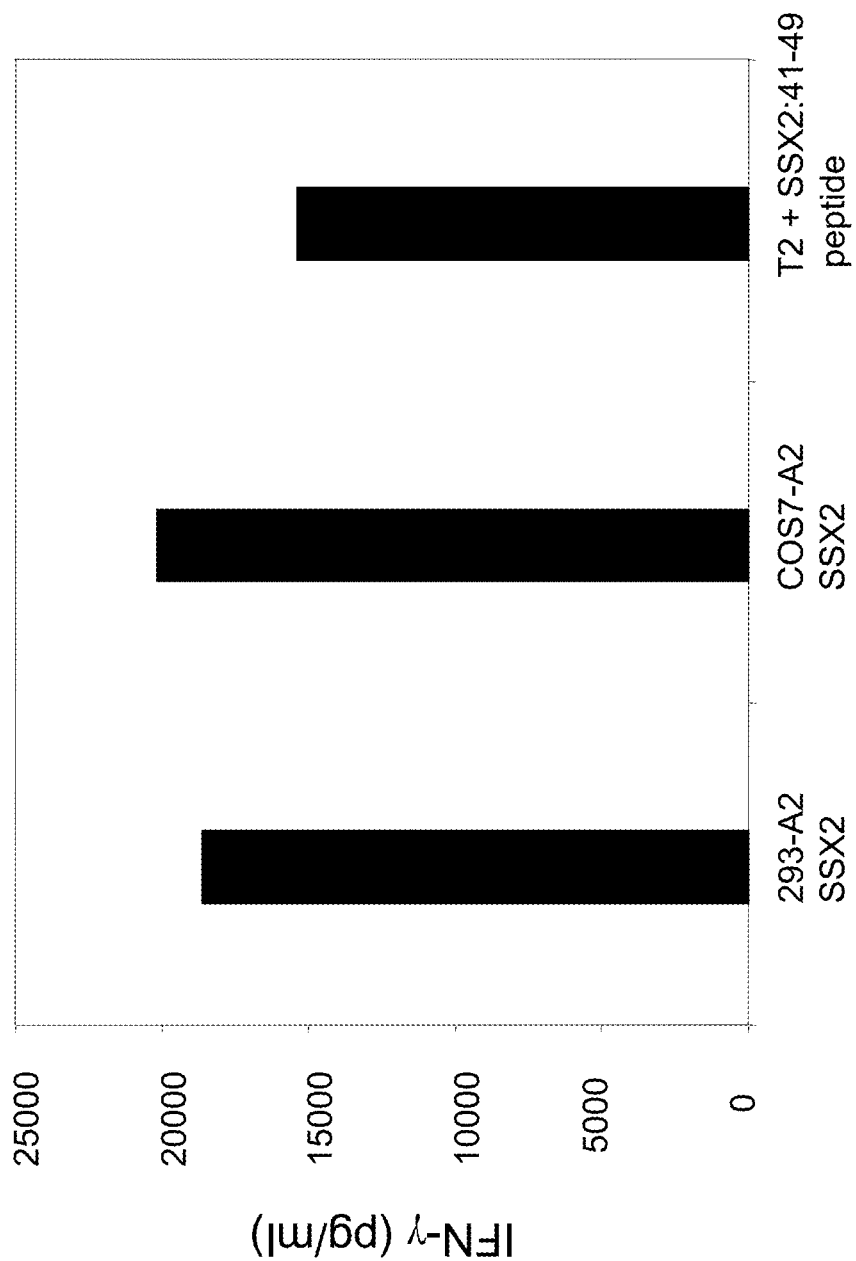

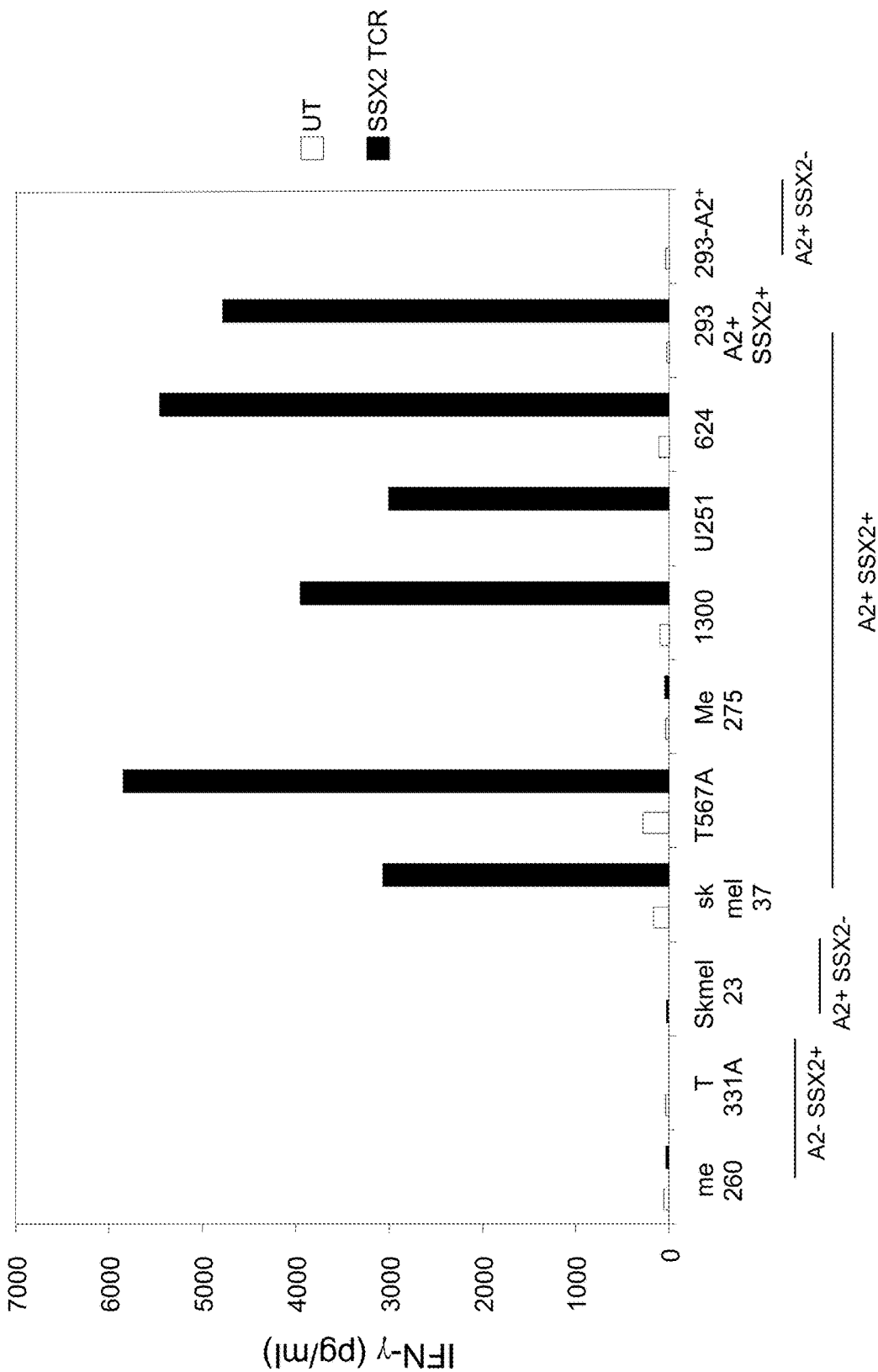

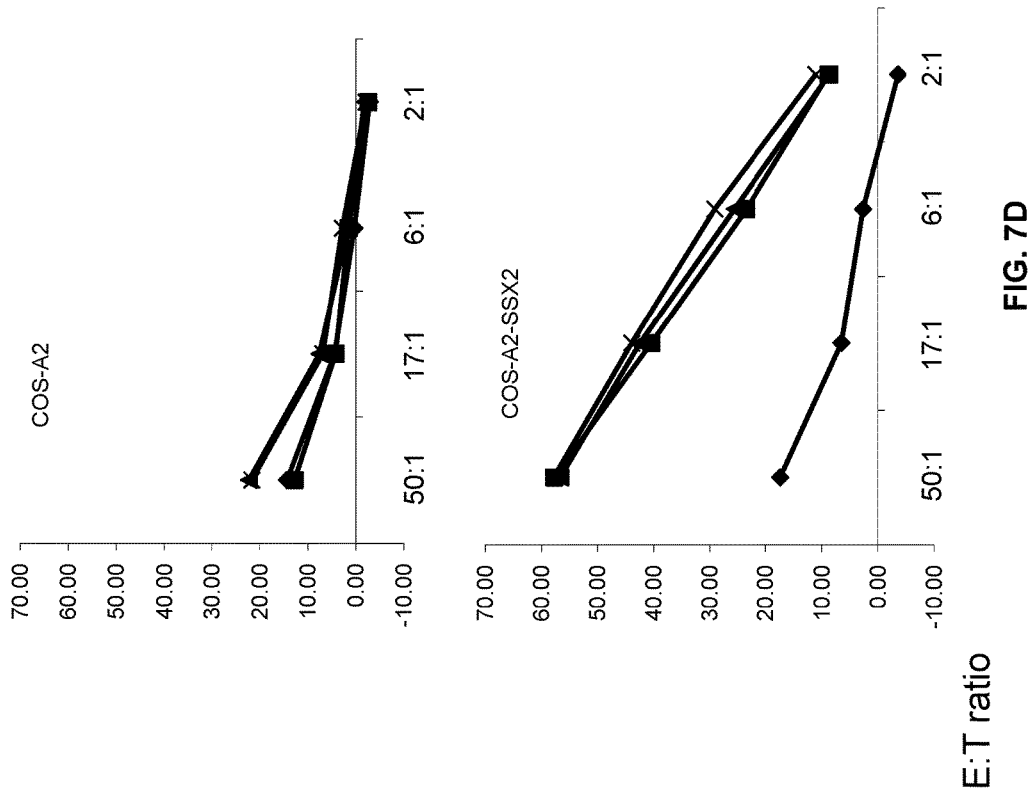
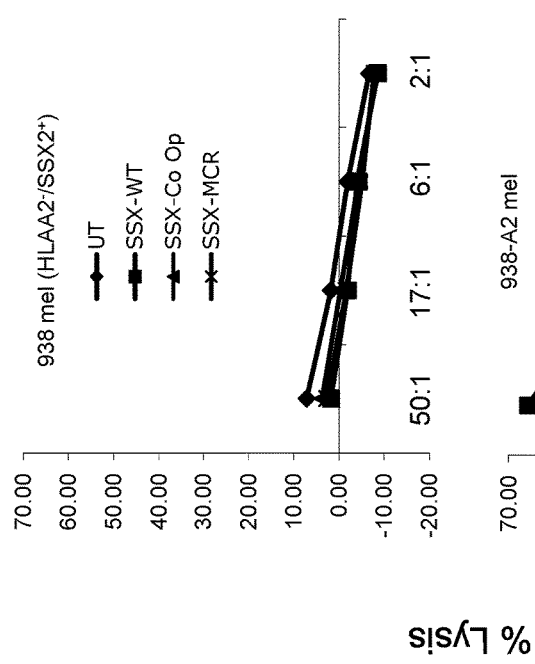
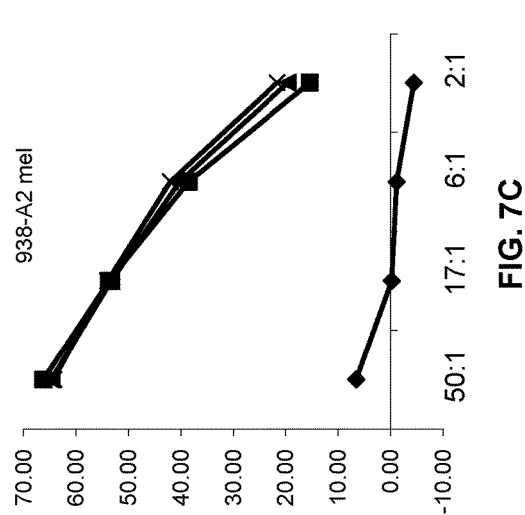
FIG. 7A, FIG. 7B, FIG. 7C, FIG. 7D

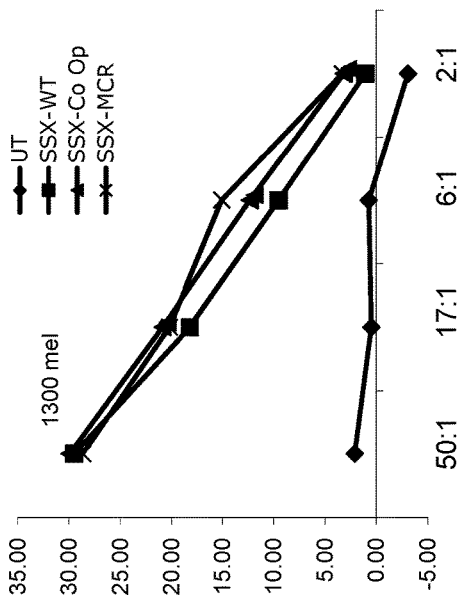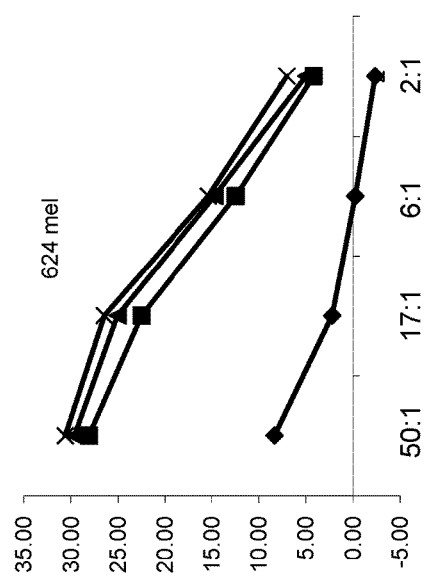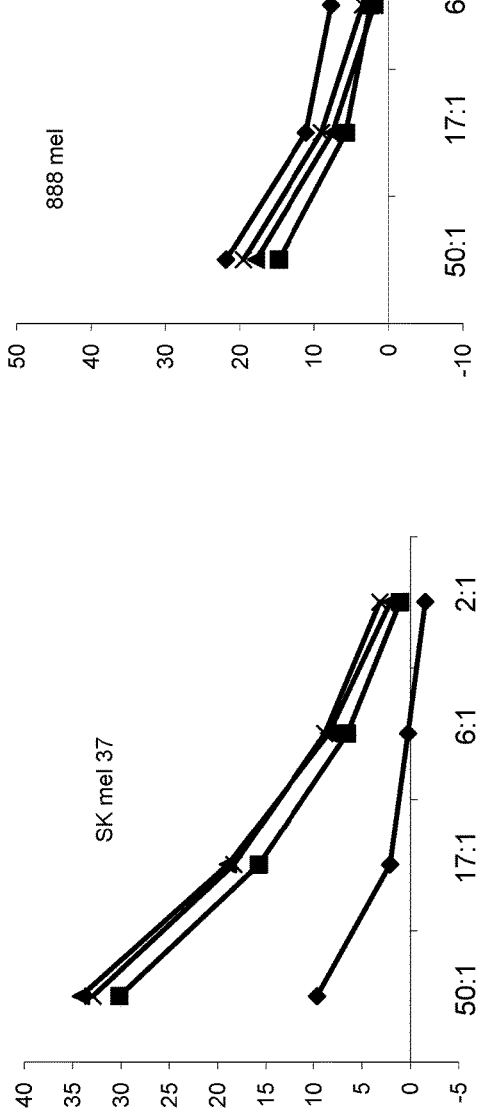

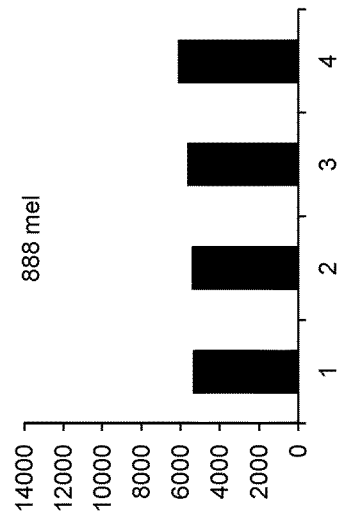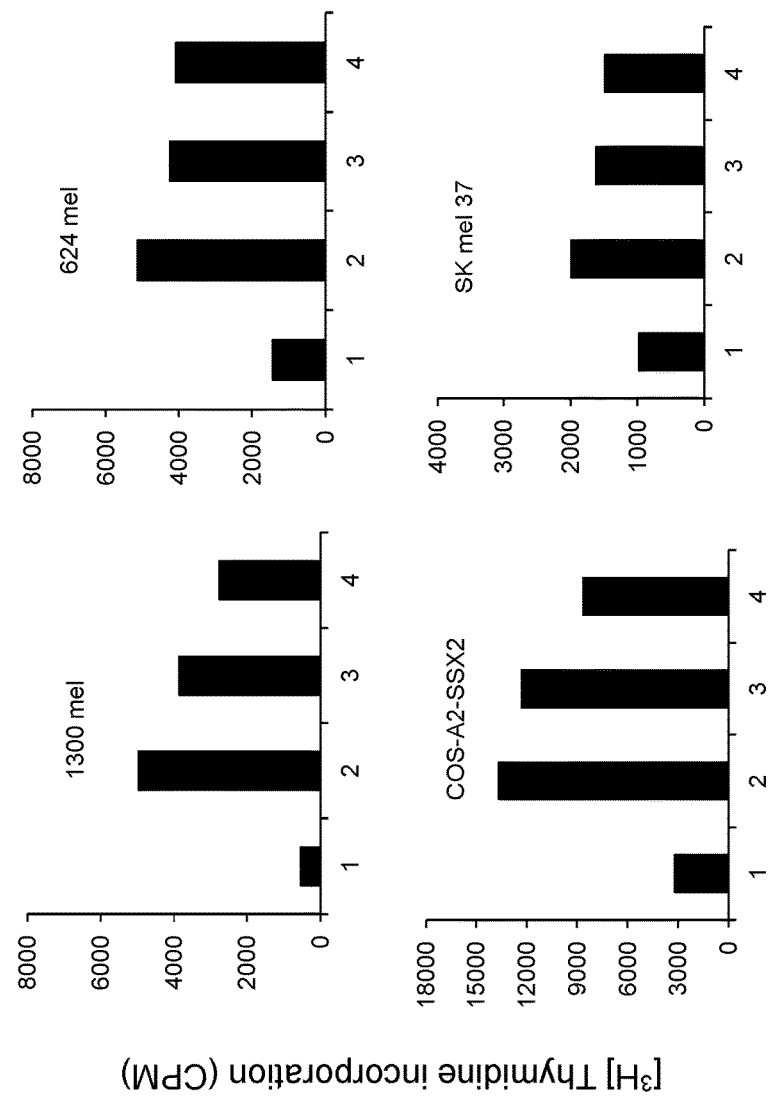

US 10,143,724 B2

ANTI-SSX-2 T CELL RECEPTORS AND RELATED MATERIALS AND METHODS OF USE

CROSS-REFERENCE TO RELATED APPLICATIONS

This patent application is a divisional of U.S. application Ser. No. 13/820,802, which is the U.S. national phase of International Patent Application No. PCT/US2011/051537, filed Sep. 14, 2011, which claims the benefit of U.S. Provisional Patent Application No. 61/384,931, filed Sep. 21, 2010, each of which is incorporated by reference in its entirety herein.

STATEMENT REGARDING FEDERALLY SPONSORED RESEARCH AND DEVELOPMENT

This invention was made with Government support under project number BC010985 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 41,570 Byte ASCII (Text) file named "723604_ST25.TXT," dated Apr. 19, 2016.

BACKGROUND OF THE INVENTION

Adoptive cell therapy (ACT) involves the transfer of reactive T cells into patients, including the transfer of tumor-reactive T cells into cancer patients. Adoptive cell therapy has been successful in causing the regression of tumors in some cancers, e.g., melanoma. One obstacle to the widespread application of adoptive cell therapy is the difficulty in generating human T cells with anti-tumor potential. Another obstacle to the successful application of adoptive cell therapy is that the transferred T cells can also be toxic to normal, i.e., non-cancerous tissues. Accordingly, there exists a need for improved immunological compositions and methods for treating cancer.

BRIEF SUMMARY OF THE INVENTION

The invention provides an isolated or purified T cell receptor (TCR) having antigenic specificity for synovial sarcoma X Breakpoint (SSX)-2 (SEQ ID NO: 1). The TCR can comprise specified amino acid sequences as described herein. For instance, the inventive TCR can comprise the amino acid sequence of any one or more of SEQ ID NOs: 13-18, SEQ ID NOs: 19 and 20, SEQ ID NOs: 23 and 24, or SEQ ID NOs: 25 and 26.

The invention further provides related polypeptides and proteins, as well as related nucleic acids, recombinant expression vectors, host cells, and populations of cells. Further provided by the invention are antibodies, or an antigen binding portion thereof, and pharmaceutical compositions relating to the TCRs of the invention.

Methods of detecting the presence of cancer in a host and methods of treating or preventing cancer in a host are further provided by the invention. The inventive method of detecting the presence of cancer in a host comprises (i) contacting a sample comprising cells of the cancer with any of the inventive TCRs, polypeptides, proteins, nucleic acids, recombinant expression vectors, host cells, populations of host cells, or antibodies, or antigen binding portions thereof, described herein, thereby forming a complex, and (ii) detecting the complex, wherein detection of the complex is indicative of the presence of cancer in the host.

The inventive method of treating or preventing cancer in a host comprises administering to the host any of the TCRs, polypeptides, or proteins described herein, any nucleic acid or recombinant expression vector comprising a nucleotide sequence encoding any of the TCRs, polypeptides, proteins described herein, or any host cell or population of host cells comprising a recombinant vector which encodes any of the TCRs, polypeptides, or proteins described herein, in an amount effective to treat or prevent cancer in the host.

BRIEF DESCRIPTION OF THE DRAWINGS

FIG. 2 is a bar graph showing IFN-γ levels measured when SSX-2 TCR-transduced PBLs were co-cultured with 293-A2 and COS7-A2 cells expressing the SSX-2 gene and T2 cells pulsed with the SSX-2: 41-49 peptide.

FIG. 4B is a bar graph that shows IFN-γ levels, as in FIG. 4A, except the PBLs were from a different human donor.

FIGS. 7A-D are graphs showing percent lysis of 938 mel (HLA-A2–/SSX-2+) (A), COS-A2 (B), 938-A2 mel (C), COS-A2-SSX-2 (D) when co-cultured with PBL that were untransduced (♦) or transduced with SSX-2 TCR (■), codon-optimized SSX-2 TCR (▲), or a codon-optimized human-mouse chimera SSX-2 TCR (X) at the indicated effector to target (E:T) ratios.

FIGS. 8A-D are line graphs showing percent lysis of 624 mel (A), 1300 mel (B), SK mel 37 (C), or 888 mel (D) when co-cultured with PBL that were untransduced (♦) or transduced with SSX-2 TCR (■), codon-optimized SSX-2 TCR (▲), or a codon-optimized human-mouse chimera SSX-2 TCR (X) at the indicated effector to target (E:T) ratios.

FIGS. 9A-9E are bar graphs showing proliferation (in terms of [$^3$H]-thymidine incorporation counts per minute (CPM)) of PBLs that were untransduced or transduced with SSX-2 TCR ("SSX-TCR-WT"), codon-optimized SSX-2 TCR ("SSX-TCR-codon optimized-PBL"), or a codon-optimized human-mouse chimera SSX-2 TCR ("SSX-2-TCR mouse constant region-PBL").

DETAILED DESCRIPTION OF THE INVENTION

Figure 1A:
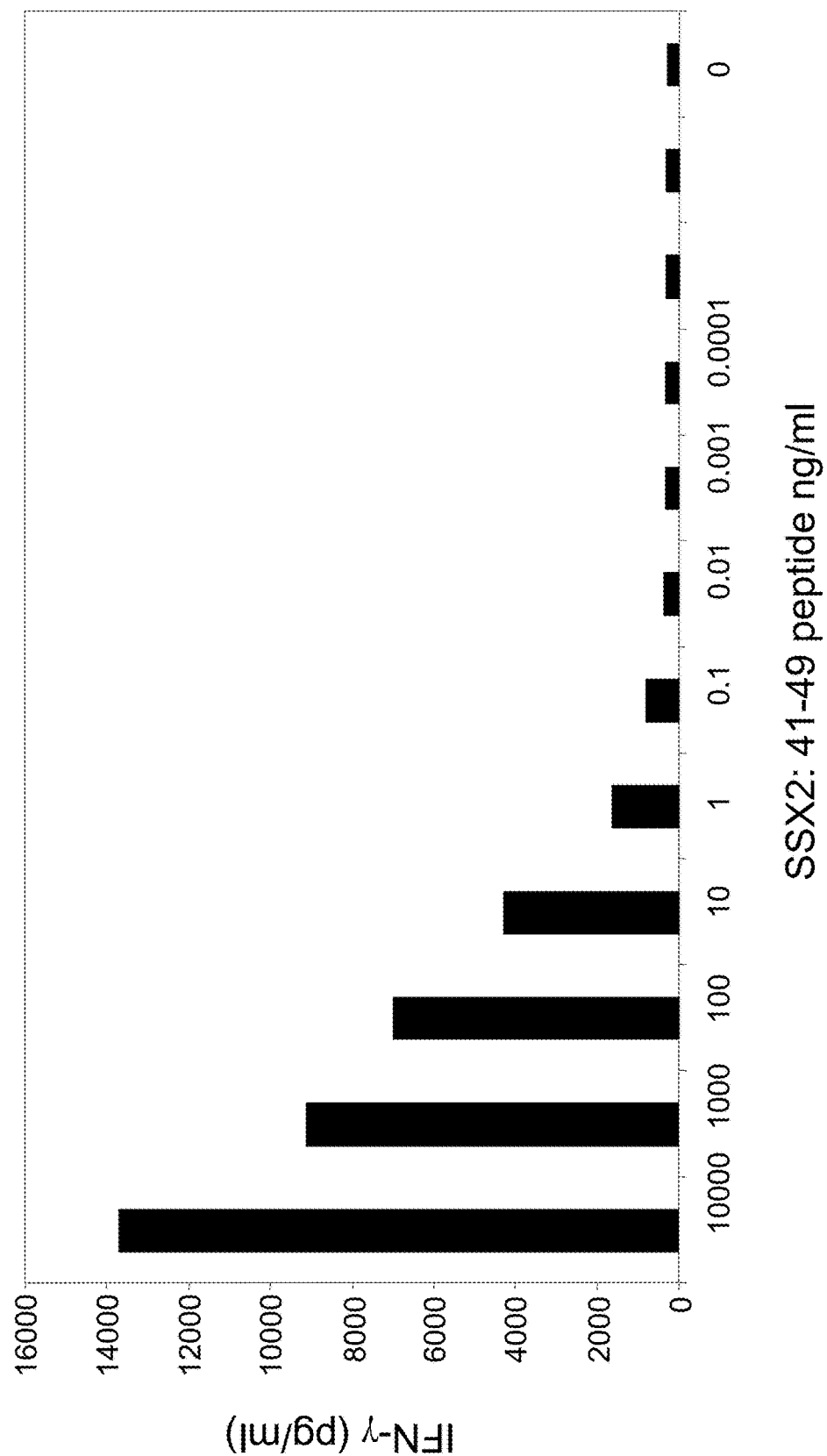
FIG. 1A is a bar graph showing interferon-γ (IFN-γ) levels measured after SSX-2 TCR-transduced peripheral blood leukocytes (PBLs) were co-cultured with T2 cells from a human donor, wherein the T2 cells were pulsed with varying concentrations of the SSX-2: 41-49 (KASEKIFYV) (SEQ ID NO: 2) peptide.

The invention provides an isolated or purified T cell receptor (TCR) having antigenic specificity for synovial sarcoma X breakpoint (SSX)-2 (also known as HOM-MEL-40). SSX-2 is a member of the SSX family of ten highly homologous nuclear proteins also including SSX-1, SSX-3, SSX-4, SSX-5, SSX-6, SSX-7, SSX-8, SSX-9, and SSX-10. The SSX proteins are cancer testis antigens (CTA), which are expressed only in tumor cells and non-MHC expressing germ cells of the testis. SSX-2 is expressed in a variety of human cancers including, but not limited to, melanomas, head cancers, neck cancers, lymphomas, multiple myeloma, pancreatic cancer, prostate cancer, sarcomas, hepatocellular and colon carcinomas. The SSX-2 protein may comprise, consist, or consist essentially of SEQ ID NO: 1.

The phrase "antigenic specificity" as used herein means that the TCR can specifically bind to and immunologically recognize SSX-2 with high avidity. For example, a TCR may be considered to have "antigenic specificity" for SSX-2 if T cells expressing the TCR secrete at least about 200 pg/ml or more (e.g., 200 pg/ml or more, 300 pg/ml or more, 400 pg/ml or more, 500 pg/ml or more, 600 pg/ml or more, 700 pg/ml or more) of IFN-γ upon co-culture with a low concentration of HLA-A2 restricted SSX-2 (e.g., about 0.01 ng/ml to about 1 ng/ml, 0.01 ng/ml, 0.1 ng/ml, or 1 ng/ml). The inventive TCRs may also secrete IFN-γ upon co-culture with higher concentrations of SSX-2.

An embodiment of the present invention includes an isolated or purified T cell receptor (TCR) having antigenic reactivity toward synovial sarcoma X Breakpoint (SSX)-2 or SSX-2 and any one or more of SSX-3, SSX-4, SSX-5, SSX-9, and SSX-10.

The TCR may have antigenic specificity for any SSX-2 protein, polypeptide or peptide. In an embodiment of the invention, the TCR has antigenic specificity for an SSX-2 protein comprising, consisting of, or consisting essentially of SEQ ID NO: 1. In a preferred embodiment of the invention, the TCR has antigenic specificity for an SSX-2 peptide comprising, consisting of, or consisting essentially of, KASEKIFYV (SEQ ID NO: 2).

While the TCRs of the invention have antigenic specificity for SSX-2, the TCRs of the invention can also recognize any one or more of SSX-3, SSX-4, SSX-5, SSX-9, and SSX-10. That is, the TCRs of the invention can bind to and immunologically recognize any one or more of SSX-3, SSX-4, SSX-5, SSX-9, and SSX-10, but with a lower avidity than that which is observed for binding to SSX-2, such that the binding of the TCR to one of these proteins elicits an immune response at a higher concentration of any one of these proteins than that which is necessary to elicit an immune response with SSX-2. For example, the TCR of the invention may be considered to recognize any one or more of SSX-3, SSX-4, SSX-5, SSX-9, and SSX-10 with low avidity if T cells expressing the TCR do not secrete at least about 200 pg/ml (e.g., secretes less than 200 pg/ml, less than 100 pg/ml) of IFN-γ upon co-culture with a low concentration of any one or more of SSX-3, SSX-4, SSX-5, SSX-9, and SSX-10 (e.g., about 0.01 ng/ml to about 1 ng/ml, 0.01 ng/ml, 0.1 ng/ml, or 1 ng/ml) but do secrete at least about 200 pg/ml or more (e.g., 200 pg/ml or more, 300 pg/ml or more, 400 pg/ml or more, 500 pg/ml or more, 600 pg/ml or more, 700 pg/ml or more) upon co-culture with a higher concentration of any one or more of SSX-3, SSX-4, SSX-5, SSX-9, and SSX-10 (e.g., about 10 ng/ml to about 100 ng/ml, 10 ng/ml, 50 ng/ml, or 100 ng/ml).

The TCR may recognize an SSX-3, SSX-4, SSX-5, SSX-9, and/or SSX-10 protein, polypeptide or peptide. In an embodiment of the invention, the TCR recognizes a protein comprising, consisting of, or consisting essentially of, SEQ ID NO: 3 (SSX-3), SEQ ID NO: 4 (SSX-4), SEQ ID NO: 5 (SSX-5), SEQ ID NO: 6 (SSX-9), and/or SEQ ID NO: 7 (SSX-10). In a preferred embodiment of the invention, the TCR recognizes a peptide comprising, consisting of, or consisting essentially of, SSX-3 peptide KVSEKIVYV (SEQ ID NO: 8), SSX-4 peptide KSSEKIVYV (SEQ ID NO: 9), SSX-5 peptide KASEKIIYV (SEQ ID NO: 10), SSX-9 peptide KSSEKIIYV (SEQ ID NO: 11), and/or SSX-10 peptide KASEKILYV (SEQ ID NO: 12).

The inventive TCRs are able to recognize SSX-2, SSX-3, SSX-4, SSX-5, SSX-9, and/or SSX-10 (hereinafter, "SSX cancer antigens") in an HLA-A2-dependent manner. By "HLA-A2-dependent manner" as used herein means that the TCR elicits an immune response upon binding to an SSX cancer antigen within the context of an HLA-A2 molecule.

Furthermore, without being bound to any particular theory, the inventive TCRs are able to recognize an SSX cancer antigen in a CD8- and/or CD4-independent manner. By "CD8- and/or CD4-independent manner," is meant that the inventive TCRs, upon binding to an SSX cancer antigen, can elicit an immune response in the absence of a CD8 or CD4 molecule, or both a CD8 and CD4 molecule, expressed on the cell expressing the inventive TCR or in the absence of a functional CD8 or CD4 molecule, or both. Unlike traditional TCRs, the inventive TCRs do not have a preference for CD8 or CD4 and can function in the context of either a CD8 or CD4 molecule.

The TCRs of the invention provide many advantages, including when used for adoptive cell transfer. For example, without being bound by a particular theory, it is believed that because SSX-2, SSX-3, SSX-4, SSX-5, SSX-9, and/or SSX-10 are expressed by cells of multiple cancer types, the inventive TCRs advantageously provide the ability to destroy cells of multiple types of cancer and, accordingly, treat or prevent multiple types of cancer. Additionally, without being bound to a particular theory, it is believed that because the SSX proteins are cancer testis antigens that are expressed only in tumor cells and non-MHC expressing germ cells of the testis, the inventive TCRs advantageously target the destruction of cancer cells while minimizing or eliminating the destruction of normal, non-cancerous cells, thereby reducing, for example, minimizing or eliminating, toxicity. In addition, while the inventive TCRs have antigenic specificity for SSX-2, the inventive TCRs advantageously also recognize any one or more of SSX-3, SSX-4, SSX-5, SSX-9, and SSX-10. Without being bound to a particular theory, it is believed that the ability to recognize multiple cancer antigens advantageously increases the number of cancer cells that can be destroyed by the inventive TCRs. Additionally, should an SSX antigen become mutated, the inventive TCRs can still be viable in that they recognize more than just one antigen.

The invention provides a TCR comprising two polypeptides (i.e., polypeptide chains), such as an α chain of a TCR, a β chain of a TCR, a γ chain of a TCR, a δ chain of a TCR, or a combination thereof. Such polypeptides chains of TCRs are known in the art. The polypeptides of the inventive TCR can comprise any amino acid sequence, provided that the TCR has antigenic specificity for SSX-2 and/or recognizes any one or more of SSX-3, SSX-4, SSX-5, SSX-9, and SSX-10.

In an embodiment of the invention, the TCR comprises two polypeptide chains, each of which comprises a variable region comprising a complementarity determining region (CDR) 1, a CDR2, and a CDR3 of a TCR. Preferably, the first polypeptide chain comprises a CDR1 comprising the amino acid sequence of SEQ ID NO: 13 (CDR1 of α chain), a CDR2 comprising the amino acid sequence of SEQ ID NO: 14 (CDR2 of α chain), and a CDR3 comprising the amino acid sequence of SEQ ID NO: 15 (CDR3 of α chain), and the second polypeptide chain comprises a CDR1 comprising the amino acid sequence of SEQ ID NO: 16 (CDR1 of β chain), a CDR2 comprising the amino acid sequence of SEQ ID NO: 17 (CDR2 of β chain), and a CDR3 comprising the amino acid sequence of SEQ ID NO: 18 (CDR3 of β chain). In this regard, the inventive TCR can comprise the amino acid sequences selected from the group consisting of any one or more of SEQ ID NOs: 13-15, 16-18, and 13-18. Preferably the TCR comprises the amino acid sequences of SEQ ID NOs: 13-18.

Alternatively or additionally, the TCR can comprise an amino acid sequence of a variable region of a TCR comprising the CDRs set forth above. In this regard, the TCR can comprise the amino acid sequence of SEQ ID NO: 19 (the variable region of an α chain) or 20 (the variable region of a β chain), both SEQ ID NOs: 19 and 20, SEQ ID NO: 35 (a portion of the variable region of an α chain) or 36 (a portion of the variable region of a β chain), or both SEQ ID NOs: 35 and 36. Preferably, the inventive TCR comprises the amino acid sequences of SEQ ID NOs: 19 and 20.

Alternatively or additionally, the TCR can comprise an α chain of a TCR and a β chain of a TCR. Each of the α chain and β chain of the inventive TCR can independently comprise any amino acid sequence. Preferably, the α chain comprises the variable region of an α chain as set forth above. In this regard, the inventive TCR can comprise the amino acid sequence of SEQ ID NO: 23. An inventive TCR of this type can be paired with any β chain of a TCR. Preferably, the β chain of the inventive TCR comprises the variable region of a β chain as set forth above. In this regard, the inventive TCR can comprise the amino acid sequence of SEQ ID NO: 24. The inventive TCR, therefore, can comprise the amino acid sequence of SEQ ID NO: 23 or 24, or both SEQ ID NOs: 23 and 24. Preferably, the inventive TCR comprises the amino acid sequences of SEQ ID NOs: 23 and 24.

In an embodiment of the invention, the TCR can comprise a human/mouse chimeric TCR. In this regard, the TCR can comprise a mouse constant region comprising SEQ ID NO: 21 (mouse constant region of an α chain), SEQ ID NO: 22 (mouse constant region of β chain), or both SEQ ID NOs: 21 and 22. Preferably, the TCR comprises both SEQ ID NOs: 21 and 22.

Alternatively or additionally, the inventive human/mouse chimeric TCR can comprise any of the CDRs set forth above. In this regard, the inventive human/mouse chimeric TCR can comprise the amino acid sequences selected from the group consisting of SEQ ID NOs: 13-15, 16-18, and 13-18. Preferably the human/mouse chimeric TCR comprises the amino acid sequences of SEQ ID NOs: 13-18.

Alternatively or additionally, the human/mouse chimeric TCR can comprise any of the variable regions set forth above. In this regard, the inventive human/mouse chimeric TCR can comprise the amino acid sequence of SEQ ID NO: 19 (the variable region of an α chain) or 20 (the variable region of a β chain), both SEQ ID NOs: 19 and 20, SEQ ID NO: 35 (a portion of the variable region of an α chain) or 36 (a portion of the variable region of a β chain), or both SEQ ID NOs: 35 and 36. Preferably, the inventive TCR comprises the amino acid sequences of SEQ ID NOs: 19 and 20.

Alternatively or additionally, the human/mouse chimeric TCR can comprise an α chain of a TCR and a β chain of a TCR. Each of the α chain and β chain of the inventive human/mouse chimeric TCR can independently comprise any amino acid sequence. Preferably, the α chain comprises the variable region of an α chain as set forth above. In this regard, the inventive human/mouse chimeric TCR can comprise the amino acid sequence of SEQ ID NO: 25. An inventive human/mouse chimeric TCR of this type can be paired with any β chain of a TCR. Preferably, the β chain of the inventive human/mouse chimeric TCR comprises the variable region of a β chain as set forth above. In this regard, the inventive human/mouse chimeric TCR can comprise the amino acid sequence of SEQ ID NO: 26. The inventive human/mouse chimeric TCR, therefore, can comprise the amino acid sequence of SEQ ID NO: 25 or 26, or both SEQ ID NOs: 25 and 26. Preferably, the inventive TCR comprises the amino acid sequences of SEQ ID NOs: 25 and 26.

Also provided by the invention is an isolated or purified polypeptide comprising a functional portion of any of the TCRs described herein. The term "polypeptide" as used herein includes oligopeptides and refers to a single chain of amino acids connected by one or more peptide bonds.

With respect to the inventive polypeptides, the functional portion can be any portion comprising contiguous amino acids of the TCR of which it is a part, provided that the functional portion specifically binds to SSX-2 and/or recognizes any one or more of SSX-3, SSX-4, SSX-5, SSX-9, and SSX-10. The term "functional portion" when used in reference to a TCR refers to any part or fragment of the TCR of the invention, which part or fragment retains the biological activity of the TCR of which it is a part (the parent TCR). Functional portions encompass, for example, those parts of a TCR that retain the ability to specifically bind to SSX-2 and/or recognize any one or more of SSX-3, SSX-4, SSX-5, SSX-9, and SSX-10 (e.g., in an HLA-A2-dependent manner), or detect, treat, or prevent cancer, to a similar extent, the same extent, or to a higher extent, as the parent TCR. In reference to the parent TCR, the functional portion can comprise, for instance, about 10%, 25%, 30%, 50%, 68%, 80%, 90%, 95%, or more, of the parent TCR.

The functional portion can comprise additional amino acids at the amino or carboxy terminus of the portion, or at both termini, which additional amino acids are not found in the amino acid sequence of the parent TCR. Desirably, the additional amino acids do not interfere with the biological function of the functional portion, e.g., specifically binding to SSX-2; recognizing any one or more of SSX-3, SSX-4, SSX-5, SSX-9, and SSX-10; having the ability to detect cancer, treat or prevent cancer, etc. More desirably, the additional amino acids enhance the biological activity, as compared to the biological activity of the parent TCR.

The polypeptide can comprise a functional portion of either or both of the α and β chains of the TCRs of the invention, such as a functional portion comprising one or more of CDR1, CDR2, and CDR3 of the variable region(s) of the α chain and/or β chain of a TCR of the invention. In this regard, the polypeptide can comprise a functional portion comprising the amino acid sequence of SEQ ID NO: 13 (CDR1 of α chain), 14 (CDR2 of α chain), 15 (CDR3 of α chain), 16 (CDR1 of β chain), 17 (CDR2 of β chain), 18 (CDR3 of β chain), or a combination thereof. Preferably, the inventive polypeptide comprises a functional portion comprising SEQ ID NOs: 13-15, 16-18, or all of SEQ ID NOs: 13-18. More preferably, the polypeptide comprises a functional portion comprising the amino acid sequences of SEQ ID NOs: 13-18.

Alternatively or additionally, the inventive polypeptide can comprise, for instance, the variable region of the inventive TCR comprising a combination of the CDR regions set forth above. In this regard, the polypeptide can comprise the amino acid sequence of SEQ ID NO: 19 (the variable region of an α chain), 20 (the variable region of a β chain), both SEQ ID NOs: 19 and 20, SEQ ID NO: 35 (a portion of the variable region of an α chain) or 36 (a portion of the variable region of a β chain), or both SEQ ID NOs: 35 and 36. Preferably, the polypeptide comprises the amino acid sequence of SEQ ID NO: 19, SEQ ID NO: 20, or the amino acid sequences of both SEQ ID NOs: 19 and 20.

Alternatively or additionally, the inventive polypeptide can comprise the entire length of an α or β chain of one of the TCRs described herein. In this regard, the inventive polypeptide can comprise an amino acid sequence of SEQ ID NOs: 23, 24, 25, or 26. Alternatively, the polypeptide of the invention can comprise α and β chains of the TCRs described herein. For example, the inventive polypeptide can comprise the amino acid sequences of both SEQ ID NOs: 23 and 24 or the sequences of both SEQ ID NOs: 25 and 26.

The invention further provides an isolated or purified protein comprising at least one of the polypeptides described herein. By "protein" is meant a molecule comprising one or more polypeptide chains.

The protein of the invention can comprise a first polypeptide chain comprising the amino acid sequence of SEQ ID NO: 19 or 35 and a second polypeptide chain comprising the amino acid sequence of SEQ ID NO: 20 or 36. The protein of the invention can, for example, comprise a first polypeptide chain comprising the amino acid sequence of SEQ ID NO: 23 or 25 and a second polypeptide chain comprising the amino acid sequence of SEQ ID NO: 24 or 26. In this instance, the protein of the invention can be a TCR. Alternatively, if, for example, the protein comprises a single polypeptide chain comprising SEQ ID NO: 23 or 25 and SEQ ID NO: 24 or 26, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. See, for instance, Choi et al., *Mol. Biotechnol.* 31: 193-202 (2005).

In some embodiments of the invention, the TCRs, polypeptides, and proteins of the invention may be expressed as a single protein comprising a linker peptide linking the α chain and the β chain. In this regard, the TCRs, polypeptides, and proteins of the invention may further comprise a linker peptide comprising an amino acid sequence comprising SEQ ID NO: 37. In an embodiment of the invention, the linker peptide may be encoded by a nucleotide sequence comprising SEQ ID NO: 38. The linker peptide may advantageously facilitate the expression of a recombinant TCR, polypeptide, and/or protein in a host cell. Upon expression of the construct including the linker peptide by a host cell, the linker peptide may be cleaved, resulting in separated α and β chains.

The protein of the invention can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or F(ab)$_2$' fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment, including any of the antibodies and antibody fragments described herein.

Included in the scope of the invention are functional variants of the inventive TCRs, polypeptides, and proteins described herein. The term "functional variant" as used herein refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to SSX-2 for which the parent TCR has antigenic specificity or to which the parent polypeptide or protein specifically binds, to a similar extent, the same extent, or to a higher extent, as the parent TCR, polypeptide, or protein. Alternatively or additionally, functional variants can also encompass, for example, those variants of the TCR, polypeptide, or protein described herein (the parent TCR, polypeptide, or protein) that retain the ability to recognize any one or more of SSX-3, SSX-4, SSX-5, SSX-9, and SSX-10, which the parent polypeptide or protein recognizes, to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 95%, 96%, 97%, 98%, 99% or more identical in amino acid sequence to the parent TCR, polypeptide, or protein.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR, polypeptide, or protein can consist essentially of the specified amino acid sequence or sequences described herein, such that other components of the functional variant, e.g., other amino acids, do not materially change the biological activity of the functional variant. In this regard, the inventive TCR, polypeptide, or protein can, for example, consist essentially of the amino acid sequence of SEQ ID NO: 23, 24, 25, 26, both SEQ ID NOs: 23 and 24, or both SEQ ID NOs: 25 and 26. Also, for instance, the inventive TCRs, polypeptides, or proteins can consist essentially of the amino acid sequence(s) of SEQ ID NO: 19, 20, 21, 22, 35, 36, both SEQ ID NOs: 19 and 20, both SEQ ID NOs: 21 and 22, or both SEQ ID NOs: 35 and 36. Furthermore, the inventive TCRs, polypeptides, or proteins can consist essentially of the amino acid sequence of SEQ ID NO: 13 (CDR1 of α chain), 14 (CDR2 of α chain), 15 (CDR3 of α chain), 16 (CDR1 of β chain), 17 (CDR2 of β chain), 18 (CDR3 of β chain), or any combination thereof, e.g., SEQ ID NOs: 13-15, 16-18, or 13-18.

The TCRs, polypeptides, and proteins of the invention (including functional portions and functional variants) can be of any length, i.e., can comprise any number of amino acids, provided that the TCRs, polypeptides, or proteins (or functional portions or functional variants thereof) retain their biological activity, e.g., the ability to specifically bind to SSX-2; recognize any one or more of SSX-3, SSX-4, SSX-5, SSX-9, and SSX-10; detect cancer in a host; or treat or prevent cancer in a host, etc. For example, the polypeptide can be 50 to 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention (including functional portions and functional variants) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

When the TCRs, polypeptides, and proteins of the invention (including functional portions and functional variants) are in the form of a salt, preferably, the polypeptides are in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The TCR, polypeptide, and/or protein of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, 3rd ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the TCRs, polypeptides, and proteins of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the TCRs, polypeptides, and/or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs, polypeptides, and proteins can be synthetic, recombinant, isolated, and/or purified.

Included in the scope of the invention are conjugates, e.g., bioconjugates, comprising any of the inventive TCRs, polypeptides, or proteins (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

Further provided by the invention is a nucleic acid comprising a nucleotide sequence encoding any of the TCRs, polypeptides, or proteins described herein (including functional portions and functional variants thereof).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the TCRs, polypeptides, or proteins, or functional portions or functional variants thereof. For example, the nucleic acid can comprise a nucleotide sequence comprising, consisting of, or consisting essentially of, SEQ ID NO: 27 (encodes anti-SSX-2 TCR alpha and beta chains) or SEQ ID NO: 28 (encodes human/mouse chimeric anti-SSX-2 TCR alpha and beta chains). The nucleotide sequence alternatively can comprise a nucleotide sequence which is degenerate to SEQ ID NO: 27 or 28.

In some embodiments, the nucleic acid sequence may be optimized. Without being bound to a particular theory, it is believed that optimization of the nucleic acid sequence increases the translation efficiency of the mRNA transcripts. Optimization of the nucleic acid sequence may involve substituting a native codon for another codon that encodes the same amino acid, but can be translated by tRNA that is more readily available within a cell, thus increasing translation efficiency. Optimization of the nucleic acid sequence may also reduce secondary mRNA structures that would interfere with translation, thus increasing translation efficiency. For example, the optimized nucleic acid can comprise a nucleotide sequence comprising, consisting of, or consisting essentially of, SEQ ID NO: 29 (encodes anti-SSX-2 TCR alpha and beta chains) or SEQ ID NO: 30 (encodes human/mouse chimeric anti-SSX-2 TCR alpha and beta chains). The nucleotide sequence alternatively can comprise a nucleotide sequence which is degenerate to SEQ ID NO: 29 or 30.

The invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transfonn or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-C1, pMAM and pMAMneo (Clontech). Preferably, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein (including functional portions and functional variants thereof), or to the nucleotide sequence which is complementary to or which hybridizes to the nucleotide sequence encoding the TCR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood leukocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, $CD4^{4+}$/$CD8^+$ double positive T cells, $CD4^+$ helper T cells, e.g., $Th_1$ and $Th_2$ cells, $CD8^+$ T cells (e.g., cytotoxic T cells), tumor infiltrating cells (TILs), memory T cells, naïve T cells, and the like. Preferably, the T cell is a $CD8^+$ T cell or a $CD4^+$ T cell.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The invention further provides an antibody, or antigen binding portion thereof, which specifically binds to a functional portion of any of the TCRs described herein. Preferably, the functional portion specifically binds to the cancer antigen, e.g., the functional portion comprising the amino acid sequence SEQ ID NO: 13 (CDR1 of α chain), 14 (CDR2 of α chain), 15 (CDR3 of α chain), 16 (CDR1 of β chain), 17 (CDR2 of β chain), 18 (CDR3 of β chain), SEQ ID NO: 19, SEQ ID NO: 20, SEQ ID NO: 35, SEQ ID NO: 36, or a combination thereof, e.g., 13-15; 16-18; 13-18; 19-20, or 35-36. More preferably, the functional portion comprises the amino acid sequences of SEQ ID NOs: 13-18. In a preferred embodiment, the antibody, or antigen binding portion thereof, binds to an epitope which is formed by all 6 CDRs (CDR1-3 of the alpha chain and CDR1-3 of the beta chain). The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive TCR. Desirably, the antibody is specific for the functional portion of the inventive TCR, such that there is minimal cross-reaction with other peptides or proteins.

Methods of testing antibodies for the ability to bind to any functional portion of the inventive TCR are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, $5^{th}$ Ed., Garland Publishing, New York, N.Y. (2001)). Alternatively, other methods, such as EBV-hybridoma methods (Haskard and Archer, *J. Immunol. Methods,* 74(2), 361-67 (1984), and Roder et al., *Methods Enzymol.*, 121, 140-67 (1986)), and bacteriophage vector expression systems (see, e.g., Huse et al., *Science,* 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display furthermore can be used to generate the antibody of the invention. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual,* $3^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.,* 235, 959-973 (1994).

The invention also provides antigen binding portions of any of the antibodies described herein. The antigen binding portion can be any portion that has at least one antigen binding site, such as Fab, $F(ab')_2$, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra).

Similarly, disulfide-stabilized variable region fragments (dsFv) can be prepared by recombinant DNA technology (see, e.g., Reiter et al., *Protein Engineering*, 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The inventive TCRs, polypeptides, proteins, (including functional portions and functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, 90% or can be 100%.

The inventive TCRs, polypeptides, proteins (including functional portions and variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, functional portions, functional variants, nucleic acids, expression vectors, host cells (including populations thereof), and antibodies (including antigen binding portions thereof), and a pharmaceutically acceptable carrier. The inventive pharmaceutical compositions containing any of the inventive TCR materials can comprise more than one inventive TCR material, e.g., a polypeptide and a nucleic acid, or two or more different TCRs. Alternatively, the pharmaceutical composition can comprise an inventive TCR material in combination with another pharmaceutically active agents or drugs, such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. The following formulations for oral, aerosol, parenteral, subcutaneous, intravenous, intramuscular, intraarterial, intrathecal, and interperitoneal administration are exemplary and are in no way limiting. More than one route can be used to administer the inventive TCR materials, and in certain instances, a particular route can provide a more immediate and more effective response than another route.

Topical formulations are well-known to those of skill in the art. Such formulations are particularly suitable in the context of the invention for application to the skin.

Formulations suitable for oral administration can consist of (a) liquid solutions, such as an effective amount of the inventive TCR material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive TCR material in a flavor, usually sucrose and acacia or tragacanth, as well as pastilles comprising the inventive TCR material in an inert base, such as gelatin and glycerin, or sucrose and acacia, emulsions, gels, and the like containing, in addition to, such excipients as are known in the art.

The inventive TCR material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive TCR material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1, 3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the inventive TCR material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)). Preferably, when administering cells, e.g., T cells, the cells are administered via injection.

It will be appreciated by one of skill in the art that, in addition to the above-described pharmaceutical compositions, the inventive TCR materials of the invention can be formulated as inclusion complexes, such as cyclodextrin inclusion complexes, or liposomes.

For purposes of the invention, the amount or dose of the inventive TCR material administered should be sufficient to effect, e.g., a therapeutic or prophylactic response, in the subject or animal over a reasonable time frame. For example, the dose of the inventive TCR material should be sufficient to bind to a cancer antigen, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, polypeptide, or protein upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the condition being treated. By way of example and not intending to limit the invention, the dose of the inventive TCR material can be about 0.001 to about 1000 mg/kg body weight of the subject being treated/day, from about 0.01 to about 10 mg/kg body weight/day, about 0.01 mg to about 1 mg/kg body weight/day.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a targeting moiety. The practice of conjugating compounds, e.g., inventive TCR materials, to targeting moieties is known in the art. See, for instance, Wadwa et al., *J. Drug Targeting* 3: 111 (1995) and U.S. Pat. No. 5,087,616. The term "targeting moiety" as used herein, refers to any molecule or agent that specifically recognizes and binds to a cell-surface receptor, such that the targeting moiety directs the delivery of the inventive TCR materials to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). The term "bridge" as used herein, refers to any agent or molecule that links the inventive TCR materials to the targeting moiety. One of ordinary skill in the art recognizes that sites on the inventive TCR materials, which are not necessary for the function of the inventive TCR materials, are ideal sites for attaching a bridge and/or a targeting moiety, provided that the bridge and/or targeting moiety, once attached to the inventive TCR materials, do(es) not interfere with the function of the inventive TCR materials, i.e., the ability to bind to SSX-2; recognize any one or more of SSX-3, SSX-4, SSX-5, SSX-9, and SSX-10; or to detect, treat, or prevent cancer.

Alternatively, the inventive TCR materials can be modified into a depot form, such that the manner in which the inventive TCR materials is released into the body to which it is administered is controlled with respect to time and location within the body (see, for example, U.S. Pat. No. 4,450,150). Depot forms of inventive TCR materials can be, for example, an implantable composition comprising the inventive TCR materials and a porous or non-porous material, such as a polymer, wherein the inventive TCR materials is encapsulated by or diffused throughout the material and/or degradation of the non-porous material. The depot is then implanted into the desired location within the body and the inventive TCR materials are released from the implant at a predetermined rate.

In an embodiment of the invention, the pharmaceutical composition further comprises 5-aza-2'-deoxycytidine (DAC). Without being bound to a particular theory, it is believed that the demethylating agent DAC enhances the recognition of cancer cells by any of the inventive TCR materials by upregulating expression of SSX-2 by cancer cells.

It is contemplated that the inventive pharmaceutical compositions, TCRs, polypeptides, proteins, nucleic acids, recombinant expression vectors, antibodies, host cells, or populations of cells can be used in methods of treating or preventing cancer. Without being bound to a particular theory, the inventive TCRs are believed to bind specifically to SSX-2 and may also recognize any one or more of SSX-3, SSX-4, SSX-5, SSX-9, and SSX-10, such that the TCR (or related inventive polypeptide or protein) when expressed by a cell is able to mediate an immune response against the cell expressing SSX-2 and may also mediate an immune response against any one or more of SSX-3, SSX-4, SSX-5, SSX-9, and SSX-10. In this regard, the invention provides a method of treating or preventing cancer in a host, comprising administering to the host any of the pharmaceutical compositions, TCRs, polypeptides, or proteins described herein, any nucleic acid or recombinant expression vector comprising a nucleotide sequence encoding any of the TCRs, polypeptides, proteins described herein, any of the antibodies described herein, or any host cell or population of cells comprising a recombinant vector which encodes any of the TCRs, polypeptides, or proteins described herein, in an amount effective to treat or prevent cancer in the host.

In an embodiment of the invention, the method of treating or preventing cancer in a host further comprises administering DAC to the host. The method may comprise administering DAC prior to, concurrently with, or after administering any of the inventive pharmaceutical compositions, TCRs, polypeptides, proteins, nucleic acids, recombinant expression vectors, host cells, or populations of cells to the host. Without being bound to a particular theory, it is believed that the demethylating agent DAC enhances the recognition of cancer cells by any of the inventive TCR materials by upregulating expression of SSX-2 by cancer cells.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Also provided is a method of detecting the presence of cancer in a host. The method comprises (i) contacting a sample comprising cells of the cancer any of the inventive TCRs, polypeptides, proteins, nucleic acids, recombinant expression vectors, host cells, populations of cells, or antibodies, or antigen binding portions thereof, described herein, thereby forming a complex, and detecting the complex, wherein detection of the complex is indicative of the presence of cancer in the host.

With respect to the inventive method of detecting cancer in a host, the sample of cells of the cancer can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting step can take place in vitro or in vivo with respect to the host. Preferably, the contacting is in vitro.

Also, detection of the complex can occur through any number of ways known in the art. For instance, the inventive TCRs, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the host. Preferably, the cells are autologous to the host.

With respect to the inventive methods, the cancer can be any cancer, including any of sarcomas (e.g., synovial sarcoma, osteogenic sarcoma, leiomyosarcoma uteri, and alveolar rhabdomyosarcoma), lymphomas (e.g., Hodgkin lymphoma and non-Hodgkin lymphoma), hepatocellular carcinoma, glioma, head-neck cancer, acute lymphocytic cancer, acute myeloid leukemia, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer (e.g., colon carcinoma), esophageal cancer, cervical cancer, gastrointestinal carcinoid tumor, hypopharynx cancer, larynx cancer, liver cancer, lung cancer, malignant mesothelioma, melanoma, multiple myeloma, nasopharynx cancer, ovarian cancer, pancreatic cancer, peritoneum, omentum, and mesentery cancer, pharynx cancer, prostate cancer, rectal cancer, renal cancer, small intestine cancer, soft tissue cancer, stomach cancer, testicular cancer, thyroid cancer, ureter cancer, and urinary bladder cancer. Of these, sarcomas (e.g., synovial sarcoma, osteogenic sarcoma, leiomyosarcoma uteri, and alveolar rhabdomyosarcoma), hepatocellular carcinoma, glioma, liver cancer, melanoma, ovarian cancer, pancreatic cancer, and prostate cancer are preferably treated.

An embodiment of the invention provides the use of any of the TCRs, polypeptides, proteins, nucleic acids, recombinant expression vectors, host cells, populations of cells, antibodies or antigen binding portions thereof, or pharmaceutical compositions, for the treatment or prevention of cancer in a host. In an embodiment, the use may further comprise the use of DAC.

The host referred to in the inventive methods can be any host. Preferably, the host is a mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but should not be construed as in any way limiting its scope.

Example 1

This example illustrates the construction of a retroviral vector for expressing SSX-2 and demonstrates SSX-2 expression in certain cell lines.

The SSX-2 gene was inserted into expression vectors pMSGV1 and pRRLSIN.cPPT.PGK. The sequence of SSX-2 inserted was:

ATGaacggagacgacgcctttgcaaggagacccacggttggtgct-
caaataccagagaagatccaaaaggccttcgat gatattgccaaatacttc-
tetaaggaagagtgggaaaagatgaaagcctcggagaaaatettetatgtg-
tatatgaagagaa
agtatgaggctatgactaaactaggtttcaaggccaccctccccacctttcat-
gtgtaataaacgggccgaagacttccaggg gaatgatttggataatgac-
cctaaccgtgggaatcaggttgaacgtcctcagatgactttggcaggctc-
cagggaatctcc
ccgaagatcatgcccaagaagccagcagaggaaggaaatgattcggag-
gaagtgccagaagcatctggcccacaaaat gatgggaaagagctgtgc-
ccccgggaaaaccaactacctctgagaagattcacgagagatctg-
gaaatagggaggcce
aagaaaaggaagagagacgcggaacagctcatcggtggagcagtca-
gaacacacacaacattggtcgattcagtttgtca acttctatgggtgcagt-
tcatggtacceccaaaacaattacacacaacagggac-
ccaaaaggggggaacatgcctggacc
cacagactgcgtgagagaaaacagctggTGA (SEQ ID NO: 31). The pRRLSIN vector also had WPRE (Woodchuck Hepatitis Virus Posttranscriptional Regulatory Element) inserted.

Expression of SSX-2 was observed by Western blot in 624.38 cells and also in COS7-A2 cells that were transduced with an SSX2 vector as above. No SSX-2 expression was observed in HSO8, Panc2551, A549, or OVCAR3 cells or non-transduced COS7-A2 cells.

SSX-2 was also measured in 938mel, U251, T567A, SKMEL23, and SKMEL37 cells. The copy number of SSX-2 normalized to β-actin is shown in Table 1.

TABLE 1

| Cell Line | Copy Number SSX-2/$10^6$ β-actin |
|---|---|
| 938mel | 17194.1 |
| U251 | 6168.2 |
| T567A | 8278.0 |
| SKMEL23 | 0.2 |
| SKMEL37 | 26568.9 |

Additional SSX-2 expression studies were performed using real time PCR. The results are shown in Table 2

TABLE 2

| Tumor cell line | Histology | Copy Number SSX-2/$10^6$ β-actin |
|---|---|---|
| Capan1 | Pancreatic cancer | 1447027 |
| CRL1837 | Pancreatic cancer | 10 |
| Panc1 | Pancreatic cancer | 255 |
| BxPC3 | Pancreatic cancer | 1653 |
| Panc2551 | Pancreatic cancer | 32641 |
| SW1990 | Pancreatic cancer | 27 |
| MiaPaca2 | Pancreatic cancer | 212 |
| HPAF-II | Pancreatic cancer | 0 |
| H766T | Pancreatic cancer | 0 |
| HPAC | Pancreatic cancer | 0 |
| H508 | Colon cancer | 5786 |
| HCT116 | Colon cancer | 0 |
| SW620 | Colon cancer | 0 |
| A549 | Lung cancer | 153 |
| H2087 | Lung cancer | 54 |
| H1299/A2 | Lung cancer | 194 |
| H2126/A2 | Lung cancer | 204 |
| H446 | Lung cancer | 550 |
| H596 | Lung cancer | 88 |
| H2066 | Lung cancer | 80 |
| H2122 | Lung cancer | 0 |
| SKLC17 | Lung cancer | 1696 |
| H82 | Lung cancer | 2303 |
| CALU6 | Lung cancer | 0 |
| H522 | Lung cancer | 1 |
| H358 | Lung cancer | 0 |
| H446 | Lung cancer | 4 |
| H1688 | Lung cancer | nd |
| H157 | Lung cancer | 0 |
| H1250 | Lung cancer | 266 |
| H2721 | Lung cancer | 75 |
| OvCar3 | Ovarian cancer | 854 |
| SKOV3 | Ovarian cancer | 739 |
| MDA-MB-231 | Breast cancer | 0 |
| MDA468 | Breast cancer | 0 |
| MCF7 | Breast cancer | 270 |
| 1300 | Melanoma | 57 |
| 1359 | Melanoma | 1391 |
| 586 | Melanoma | 327 |
| 888 | Melanoma | 137 |
| 624.38 | Melanoma | 915 |
| 2984 | Melanoma | 111 |
| 526-NY-ESO | Melanoma | 0 |
| SKMEL23 | Melanoma | 1 |
| SKMEL37 | Melanoma | 18833 |
| T567A | Melanoma | 7426 |
| T331A | Melanoma | 4 |
| [redacted name of cell donor] | Renal cancer | 193 |
| Toledo | Lymphoma | 166 |
| NALM6 | Leukemia | 0 |
| U251 | Glioma | 25642 |
| 397/A2 | | 10782 |
| SK-N-AS | Neuroblastoma | 1 |
| PBL | Normal lymphocytes | 36 |
| 293GP | | 0 |
| 293-SSX2/A2+ | | 478175 |
| COS7 | | 0 |
| COS-SSX2/A2+ | | 616981 |

Example 2

This example illustrates the construction of a retroviral vector for expressing an SSX-2 specific TCR.

An HLA-A2 restricted TCR from a natural T cell clone was isolated using 5'-RACE from a tumor-infiltrated lymph node (TILN) from a melanoma patient seropositive for SSX-2 and whose tumor expressed SSX-2.

The T cell clone showed: TRAV14/DV4*01 (number of bacterial clones positive 21/23) and TRBV15*02-CB1 (number of bacterial clones positive 23/23).

A retroviral vector was constructed expressing the TCR α and β chains incorporating the 2a cleavage peptide. Separate PCR reactions for the α chain and the β chain were performed. For the α chain, the forward primer incorporated an NcoI restriction site of ATG. The reverse primer had furin-SGSG-P2a incorporated before the recognition sequence. For the β chain, the forward primer also incorporated furin-SGSG-P2a before the recognition sequence, and the reverse primer had a stop codon and NotI restriction site.

Upon completion, the separate PCR reactions were combined and additional PCR performed with outside primers to generate an α chain (TRAV14)-linker-β chain (TRBV15-CB1) construct. The construct contained SEQ ID NO: 27, encoding anti-SSX-2 TCR alpha and beta chains.

The construct was cloned into the pMSGV1 retroviral vector using the NcoI and NotI restriction sites.

Example 3

This example demonstrates that PBLs engineered with a SSX-2 TCR show SSX-2 peptide specific reactivity and tetramer binding.

Human donor-derived PBLs were transduced with the SSX-2 TCR vector of Example 2 and tested for peptide reactivity and tetramer binding.

Tetramer binding was observed in CD4 and CD8 cells.

Figure 1B:
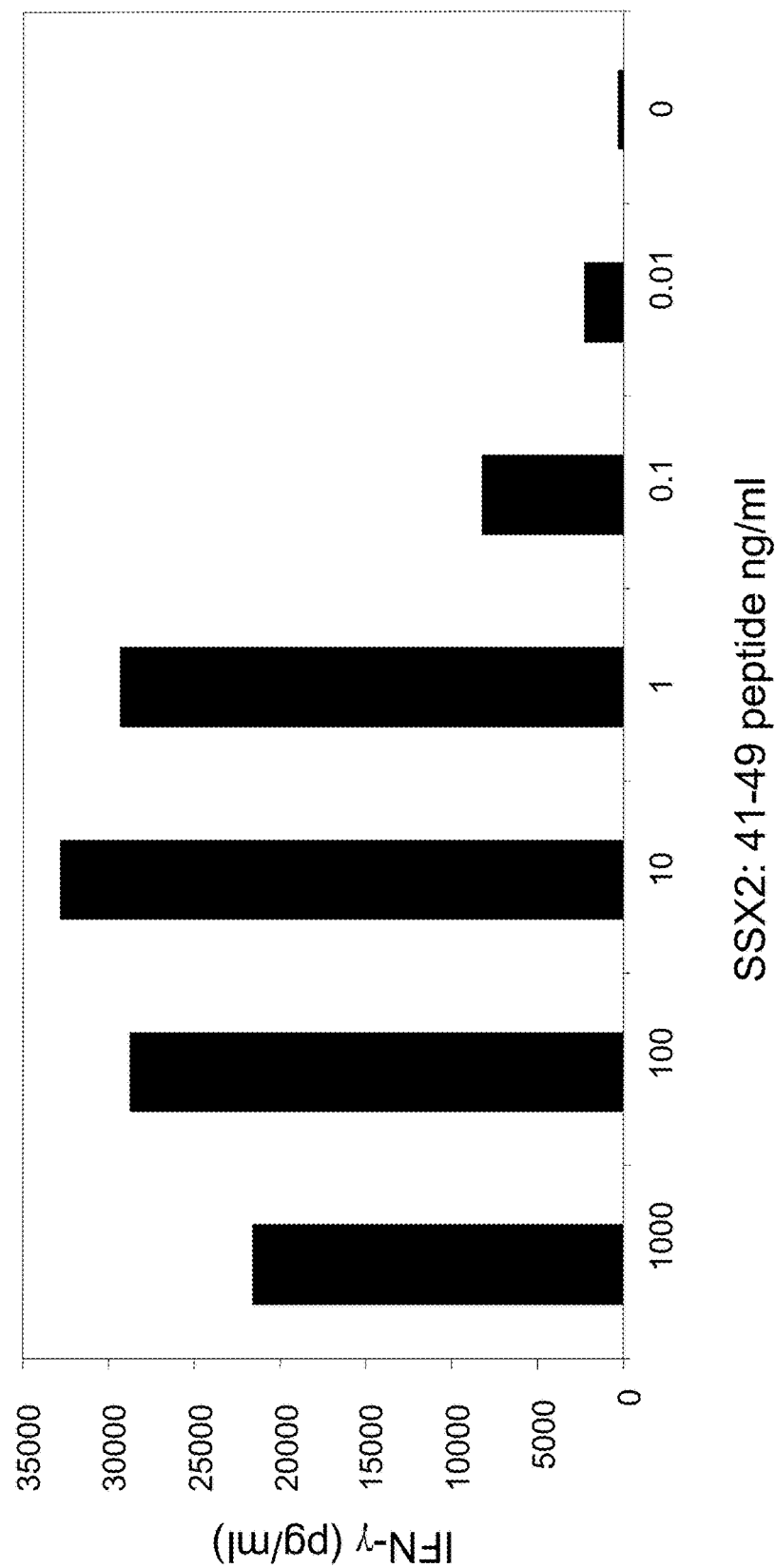
FIG. 1B is a bar graph showing IFN-γ levels measured, as in FIG. 1A, except the T2 cells were from a different human donor.

SSX-2 TCR-transduced PBLs were co-cultured with T2 cells from two human donors, where the T2 cells were pulsed with varying concentrations of the SSX-2: 41-49 (KASEKIFYV) peptide. FIGS. 1A and 1B show the resulting interferon-γ levels (pg/ml) measured. These data show that SSX-2 TCR-transduced PBLs recognize SSX-2: 41-49 peptide down to 0.01 ng/ml, or less. The differences between FIGS. 1A and 1B may be due to donor variability.

SSX-2 TCR-transduced PBLs were also co-cultured with cells from Example 1 retrovirally engineered to express the SSX-2 gene. FIG. 2 shows the resulting interferon-γ levels (pg/ml) measured when the PBLs were co-cultured with 293-A2 and COST-A2 cells expressing the SSX-2 gene and T2 cells pulsed with the SSX-2: 41-49 peptide. PBLs that were not transduced with a SSX-2 TCR showed no reactivity against these cells.

Example 4

This example demonstrates that PBLs engineered with the SSX-2 TCR of Example 2 show reactivity against tumor cell lines.

Figure 3:
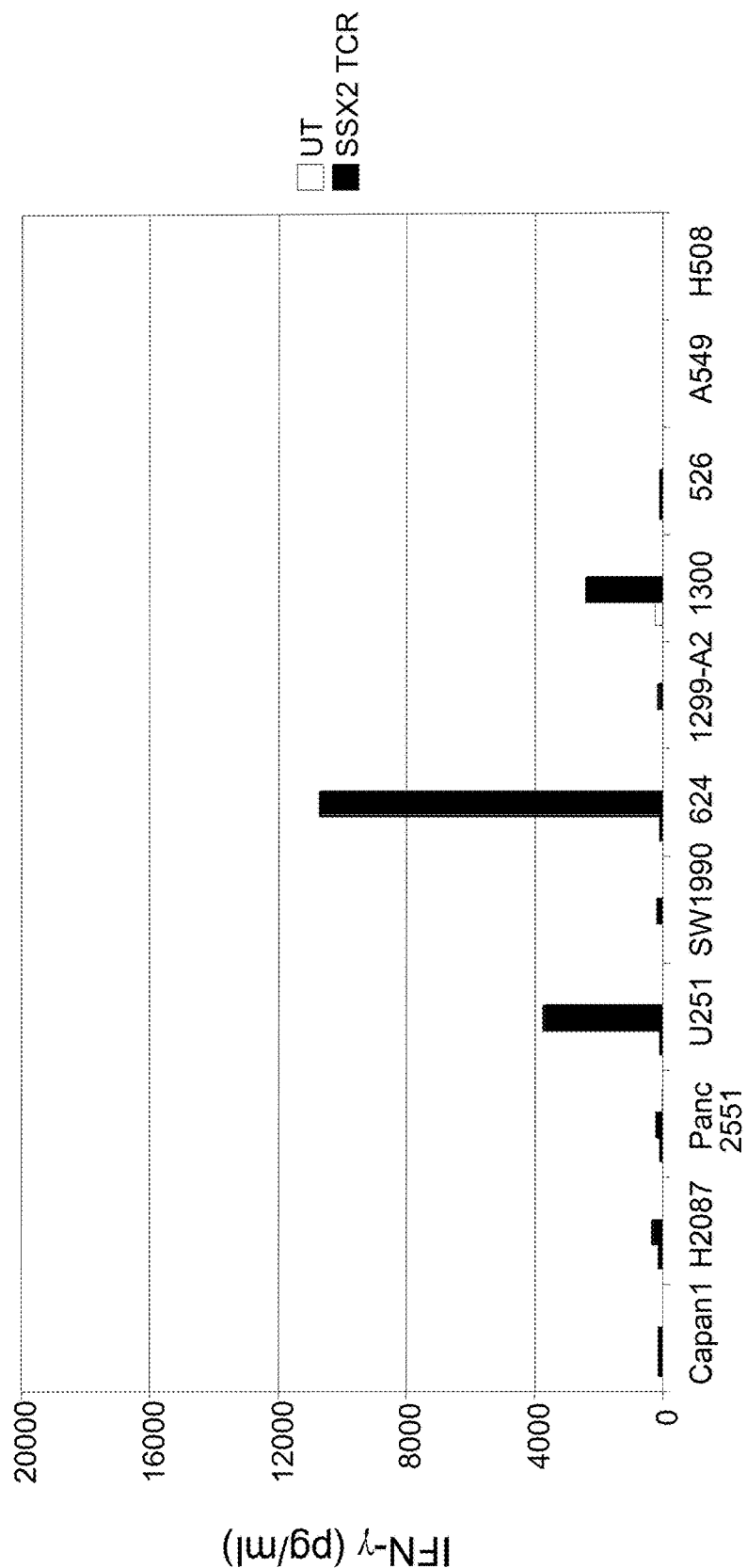
FIG. 3 is a bar graph that shows the resulting IFN-γ levels measured when SSX-2 TCR-transduced PBLs (shaded bars) or untransduced (UT) PBLs (unshaded bars) were co-cultured with various tumor cell lines.

SSX-2 TCR-transduced PBLs were co-cultured with various tumor cell lines. FIG. 3 shows the resulting interferon-γ levels (pg/ml) measured. These data show that SSX-2 TCR engineered T cells recognized naturally processed and presented SSX-2 protein in both melanoma (624, and 1300) and glioblastoma cell lines (U251). PBLs that were not transduced with a SSX-2 TCR (UT) showed very little or no reactivity.

Figure 4A:
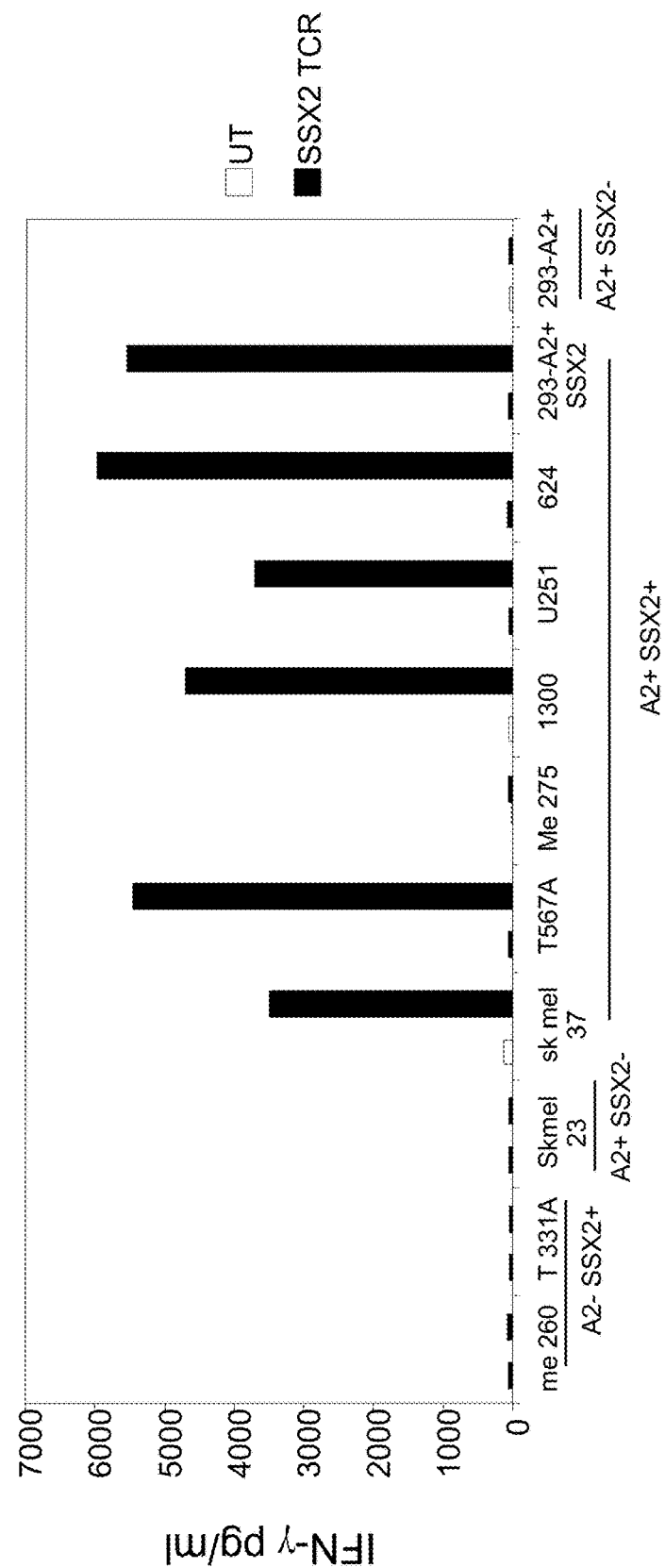
FIG. 4A is a bar graph that shows IFN-γ levels after PBLs from a human donor, that were transduced with a SSX-2 TCR (shaded bars) or not transduced (UT) (unshaded bars), were co-cultured with various tumor cells.
Figure 11:
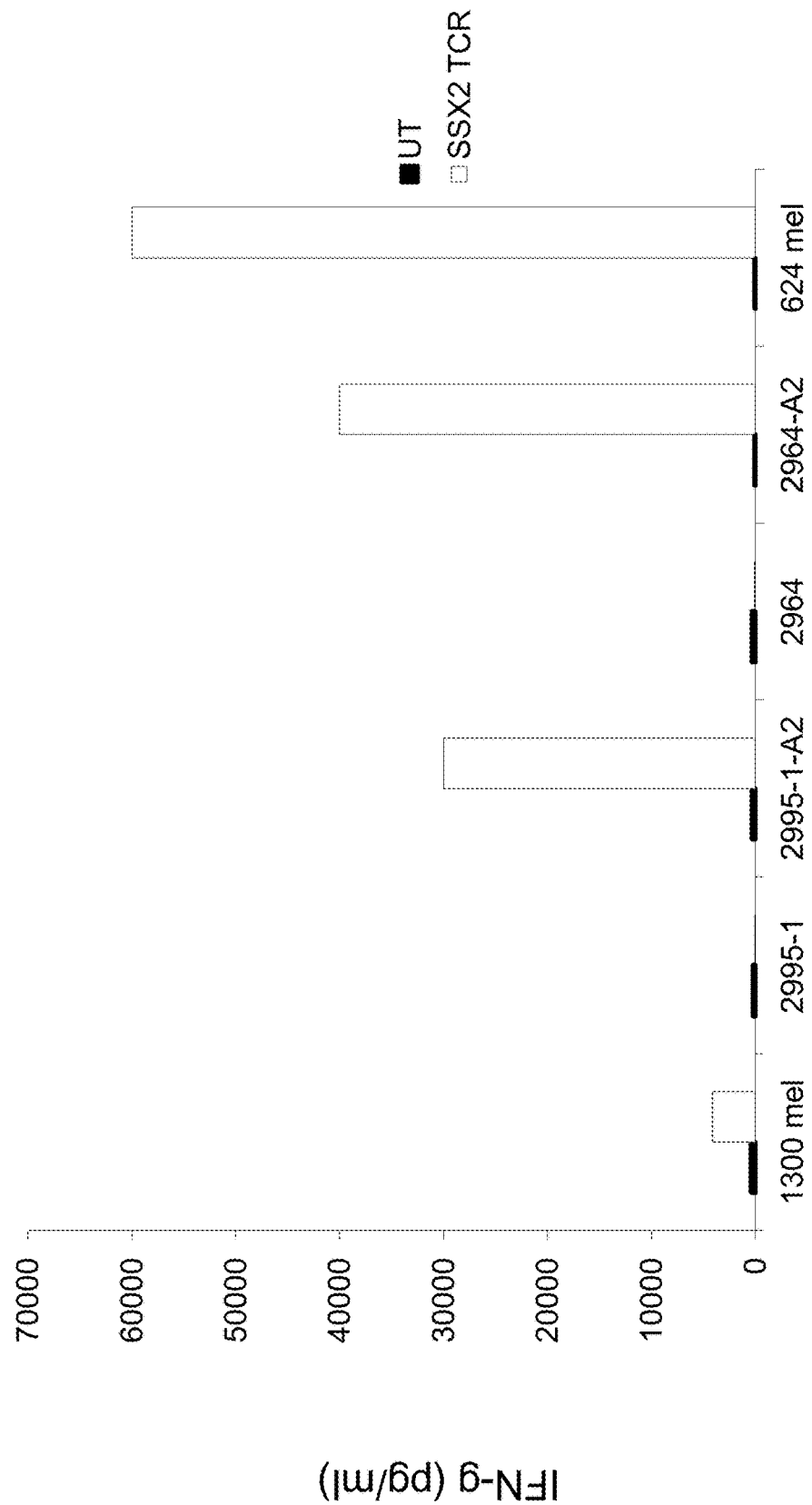
FIG. 11 is a bar graph that shows IFN-γ levels after PBLs from a human donor, that were transduced with a SSX-2 TCR (unshaded bars) or not transduced (UT) (shaded bars), were co-cultured with various primary melanoma cells.

FIGS. 4A and 4B, FIG. 11, and Tables 3 and 4 show additional results of PBLs from human donors that were transduced with the SSX-2 TCR of Example 2 when these PBLs were co-cultured with various tumor cells.

TABLE 3

| Cell line | Histology | UT IFN-γ (pg/ml) | SSX2-TCR IFN-γ (pg/ml) |
|---|---|---|---|
| COS-A2 | | 144 | 297 |
| 293-A2 | | 25 | 173 |
| 888 | | 45 | 126 |
| OVCAR3 | | 0 | 0 |
| MCF7 | | 0 | 0 |
| SKMEL 23 | | 0 | 0 |
| T331A | | 0 | 0 |
| COS-A2 SSX2 | | 71 | 36070 |
| 624 | Melanoma | 0 | 26515 |
| 938-A2 | Melanoma | 0 | 19320 |
| 938 | | 0 | 0 |
| 293-A2 SSX2 | | 0 | 33913 |
| U251 | Glioma | 0 | 9770 |
| SK MEL37 | Melanoma | 188 | 10000 |
| SKOV3 | Ovarian | 0 | 663 |
| H82 | | 0 | 141 |
| HEPG2 | | 0 | 25 |
| T567A | Melanoma | 152 | 10280 |
| MEDIUM | | 0 | 0 |

TABLE 4

| Cell line | Histology | UT IFN-γ (pg/ml) | SSX2-TCR IFN-γ (pg/ml) |
|---|---|---|---|
| COS-A2 | | 280 | 180 |
| 293-A2 | | 112 | 144 |
| 888 | | 115 | 143 |
| OVCAR3 | | 8 | 21 |
| MCF7 | | 74 | 3 |
| SKMEL 23 | | 6 | 0 |
| T331A | | 122 | 42 |
| COS-A2 SSX2 | | 123 | 56820 |
| 624 | Melanoma | 0 | 21730 |
| 938-A2 | Melanoma | 38 | 19192 |
| 938 | | 0 | 0 |
| 293-A2 SSX2 | | 125 | 20595 |
| U251 | Glioma | 0 | 12025 |
| SK MEL37 | Melanoma | 313 | 9720 |
| SKOV3 | Ovarian | 93 | 610 |
| H82 | | 0 | 100 |
| HEPG2 | | 73 | 61 |
| T567A | Melanoma | 382 | 13245 |
| MEDIUM | | 25 | 0 |

Example 5

This example demonstrates that PBLs engineered with a SSX-2 TCR show reactivity against other SSX protein peptides.

Co-culture assays were performed with PBLs transduced with the SSX-2 TCR of Example 2 and peptide-pulsed T2 cells.

Figure 5:
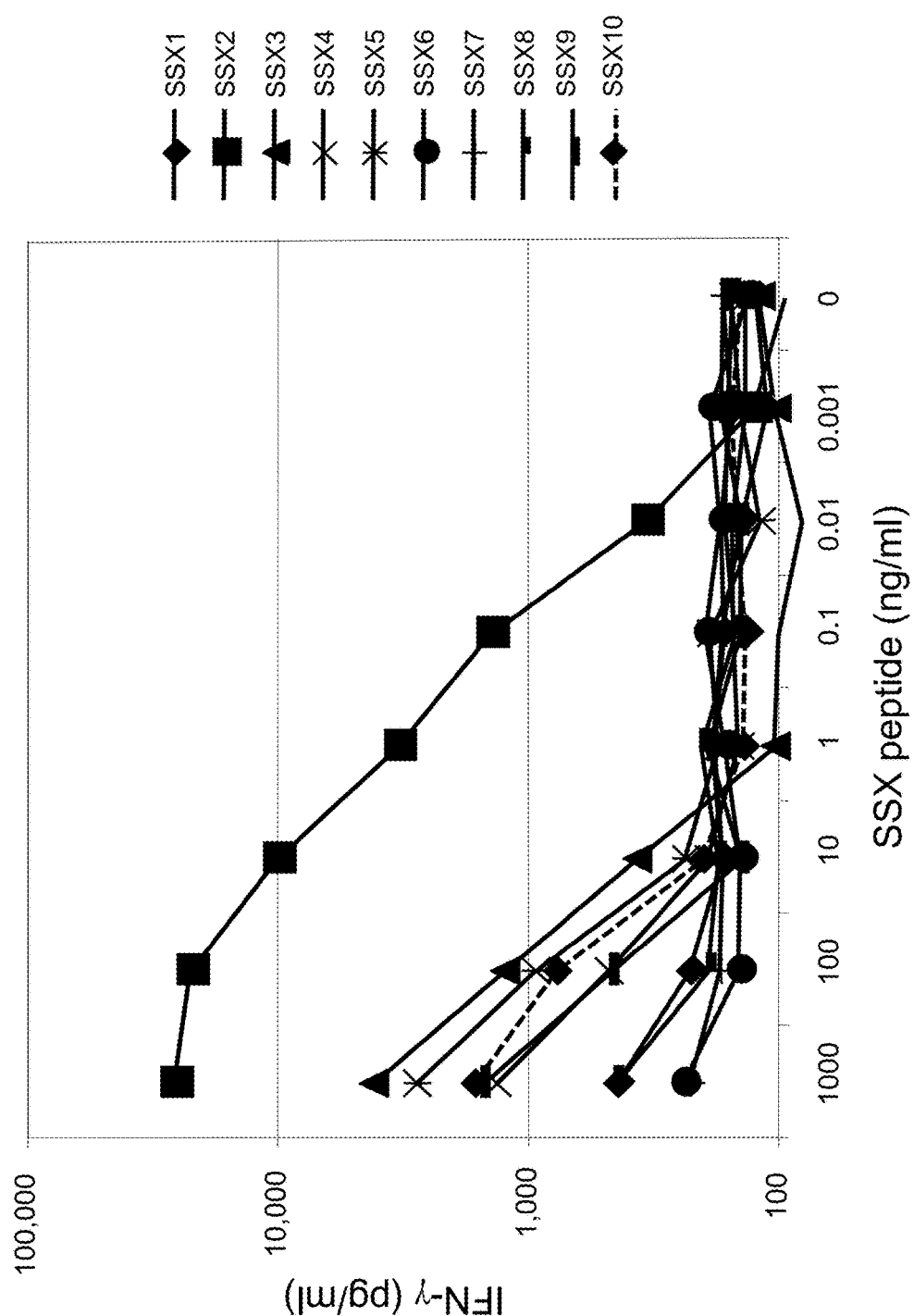
FIG. 5 is a line graph that shows the results of co-culture assays performed with SSX-2 TCR transduced-PBLs and peptide-pulsed T2 cells. The peptides used for pulsing were: SSX-1 (KYSEKISYV, SEQ ID NO: 32) (—♦—); SSX-2 (KASEKIFYV, SEQ ID NO: 2) (■); SSX-3 (KVSEKIVYV, SEQ ID NO: 8) (▲); SSX-4 (KSSEKIVYV, SEQ ID NO: 9) (X); SSX-5 (KASEKIIYV, SEQ ID NO: 10) (*); SSX-6 (KFSEKISCV, SEQ ID NO: 33) (●); SSX-7 (KSLEKISYV, SEQ ID NO: 34) (|); SSX-8 KYSEKISYV, SEQ ID NO: 32) (-); SSX-9 (KSSEKIIYV, SEQ ID NO: 11) (—); and SSX-10 (KASEKILYV, SEQ ID NO: 12) (—♦—).

FIG. 5 shows the SSX-2 TCR is most reactive with the peptide of SSX-2 and also recognizes the peptides of SSX-3, -4, -5, -9, and -10 over the other SSX peptides, although greater recognition is seen at higher peptide concentrations.

Example 6

This example demonstrates that codon optimization and introduction of a mouse constant region improved the expression and function of SSX-2 TCR in human PBLs.

Human PBL were untransduced or transduced with a vector comprising SEQ ID NO: 27 (SSX-2 TCR), SEQ ID NO: 29 (codon-optimized SSX-2 TCR), or SEQ ID NO: 30 (codon-optimized SSX-2 TCR including mouse constant region). Expression was measured by FACS analysis. Mean fluorescence intensity was measured to be 656 for cells transduced with SEQ ID NO: 27 (SSX-2 TCR), 910 for cells transduced with SEQ ID NO: 29 (codon-optimized SSX-2 TCR), and 949 for cells transduced with SEQ ID NO: 30 (codon-optimized SSX-2 TCR including mouse constant region).

In another experiment, measurement of tetramer binding confirmed that codon optimization and introduction of a mouse constant region improved the expression of SSX-2 TCR in human PBLs.

In another experiment, FACS analysis also revealed that the activation marker CD137 (4-1BB) was upregulated following co-culture of human PBL transduced with SEQ ID NO: 27 (SSX-2 TCR), SEQ ID NO: 29 (codon-optimized SSX-2 TCR), or SEQ ID NO: 30 (codon-optimized SSX-2 TCR including mouse constant region) with COS-A2-SSX2 cells.

Another experiment evaluated the function of the SSX-2 TCRs by measuring CD107a mobilization following coculture with COS-A2-SSX-2 cells. On Day 0, PBL were stimulated with OKT3. On Day 2, the PBL were transduced as described in this example. On Day 15, the PBL were co-cultured for 2 hours with COS-A2 cells or COS-A2-SSX-2 cells. On Day 16, CD107a mobilization was measured by FACS analysis. The results showed that codon optimization and introduction of a mouse constant region improved the function of SSX-2 TCR as measured by CD107a mobilization following co-culture with COS-A2-SSX-2 cells.

The function of the SSX-2 TCRs was also measured by IL-2 and IFN-γ production following co-culture with COS-A2-SSX-2 cells or 938-A2 mel cells. PBL were stimulated with OKT3 and transduced as described in this example. On Day 10, the PBL were co-cultured with COS-A2 cells, COS-A2-SSX-2 cells, 938-A2 mel cells, or 938mel cells. On Day 11, IL-2 and IFN-γ production was measured by FACS analysis. The results showed that codon optimization and introduction of a mouse constant region improved the function of SSX-2 TCR as measured by IL-2 and IFN-γ production following co-culture with COS-A2-SSX-2 cells and 938-A2 mel cells.

Example 7

This example demonstrates that PBLs engineered with the SSX-2 TCR, codon-optimized SSX-2 TCR, or a codon-optimized human-mouse chimera SSX-2 TCR show reactivity against tumor cell lines.

PBLs that were untransduced (UT) or transduced with a vector comprising SEQ ID NO: 27 (SSX-2 TCR), SEQ ID NO: 29 (codon-optimized SSX-2 TCR), or SEQ ID NO: 30 (codon-optimized SSX-2 TCR including mouse constant region) were co-cultured with various tumor cell lines. Tables 5 and 6 show the resulting interferon-γ levels (pg/ml) measured with respect to PBL from two different donors. These data show that the transduced T cells recognized naturally processed and presented SSX-2 protein in multiple tumor cell lines. PBLs that were not transduced with a SSX-2 TCR (UT) showed very little or no reactivity.

TABLE 5

| Cell line | UT | SSX2-TCR-WT (SEQ ID NO: 27) | SSX2-TCR-Co Op (SEQ ID NO: 29) | SSX2-TCR-MCR (SEQ ID NO: 30) |
| --- | --- | --- | --- | --- |
| T cell alone | 445 | 165 | 164 | 327 |
| K562 | 1950 | 1969 | 1714 | 2752 |
| Lau 149 mel | 925 | 285 | 193 | 270 |
| T331A mel | 47 | 30 | 30 | 30 |
| Cos-A2 | 1280 | 2839 | 2338 | 2827 |
| 293-A2 | 1234 | 582 | 711 | 802 |
| 938 mel | 1117 | 1239 | 890 | 1122 |
| COS-A2-SSX2 | 615 | 52577 | 64142 | 56893 |
| 293-A2-SSX2 | 515 | 29804 | 37522 | 37258 |
| K562-A2-Erythroleukemia | 1830 | 12542 | 21325 | 17437 |
| Skmel 37 mel | 96 | 6635 | 8869 | 10401 |
| 1300 mel | 176 | 2556 | 2596 | 2715 |
| 624 mel | 453 | 27344 | 37547 | 46999 |
| 938-A2 mel | 626 | 37032 | 46304 | 51092 |
| U251 Glioma | 372 | 16653 | 19223 | 19027 |
| SKOV3 Ovarian | 877 | 2414 | 2527 | 2221 |

TABLE 6

| Cell line | UT | SSX2-TCR-WT | SSX2-TCR-Co Op | SSX2-TCR-MCR |
| --- | --- | --- | --- | --- |
| T cell alone | 180 | 322 | 290 | 554 |
| K562 | 1734 | 1807 | 2784 | 3328 |
| Lau 149 mel | 124 | 125 | 120 | 142 |
| T331A mel | 115 | 58 | 30 | 38 |
| Cos-A2 | 252 | 460 | 601 | 553 |
| 293-A2 | 994 | 1520 | 1067 | 1005 |
| 938 mel | 915 | 1451 | 768 | 932 |
| COS-A2-SSX2 | 65 | 85892 | 138324 | 164314 |
| 293-A2-SSX2 | 1027 | 52481 | 49112 | 47273 |
| K562-A2-Erythroleukemia | 1945 | 12825 | 13610 | 13555 |
| Skmel 37 | 232 | 8941 | 11445 | 10630 |
| 1300 mel | 258 | 3162 | 3052 | 3460 |
| 624 mel | 2340 | 60174 | 47059 | 57693 |
| 938-A2 mel | 2175 | 46094 | 51173 | 40047 |
| U251 Glioma | 656 | 22888 | 21418 | 20027 |
| SKOV3 Ovarian | 652 | 10953 | 22509 | 9857 |

Example 8

This example demonstrates that PBLs engineered with the SSX-2 TCR, codon-optimized SSX-2 TCR, or a codon-optimized human-mouse chimera SSX-2 TCR proliferate upon co-culture with SSX2+/HLA-A2+ target cells.

Figure 6A:
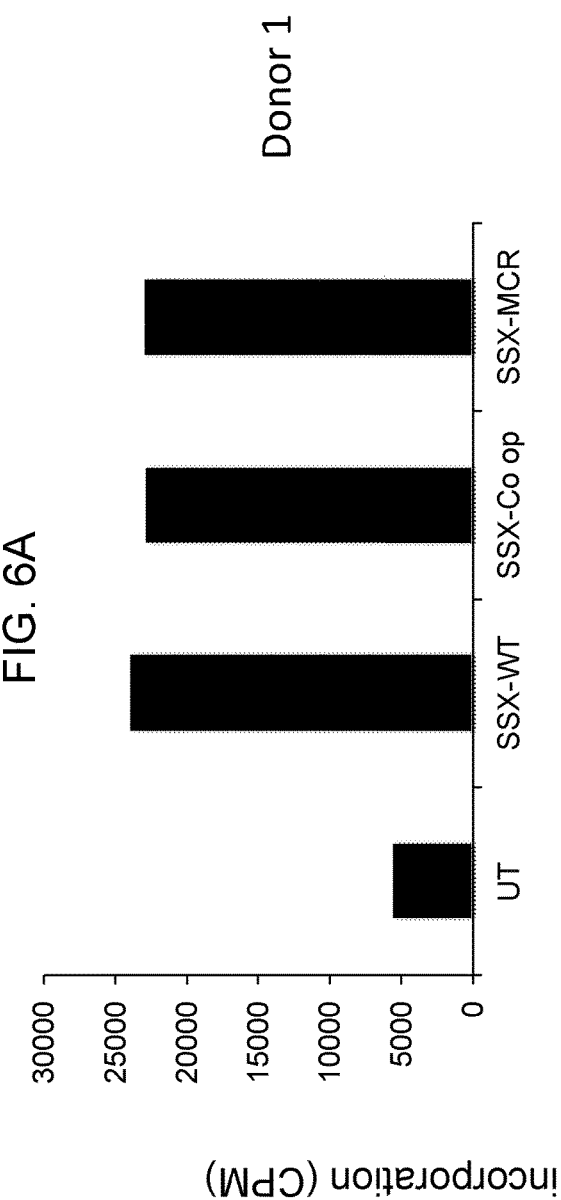
FIGS. 6A and 6B are bar graphs showing proliferation (in terms of [$^3$H]-thymidine incorporation counts per minute (CPM)) of PBLs from Donor 1 (A) or Donor 2 (B) that were untransduced (UT) or transduced with SSX-2 TCR ("SSX-WT"), codon-optimized SSX-2 TCR ("SSX-CO op"), or a codon-optimized human-mouse chimera SSX-2 TCR ("SSX-MCR").
Figure 6B:
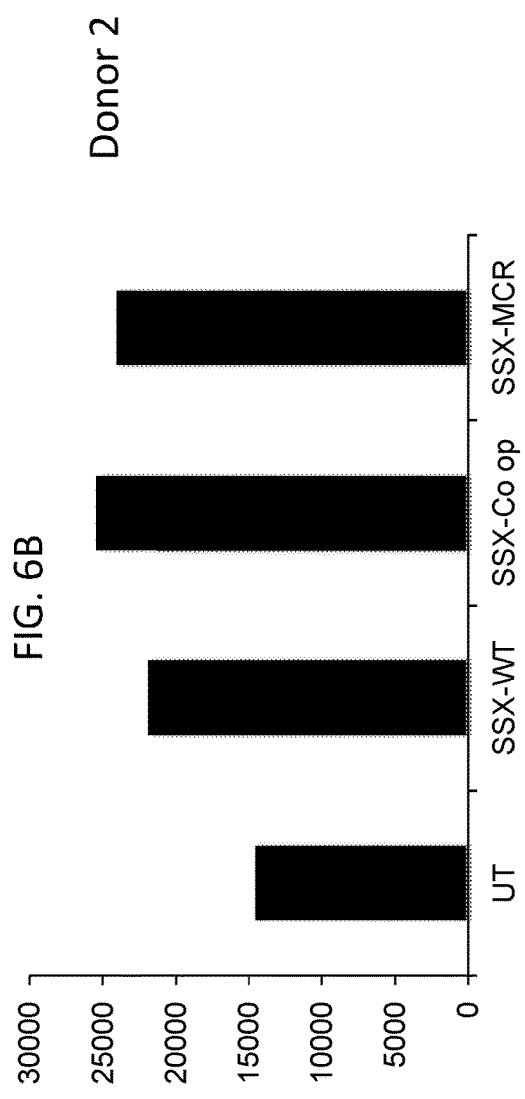

PBLs from Donor 1 or Donor 2 that were untransduced (UT) or transduced with a vector comprising SEQ ID NO: 27 (SSX-2 TCR), SEQ ID NO: 29 (codon-optimized SSX-2 TCR), or SEQ ID NO: 30 (codon-optimized SSX-2 TCR including mouse constant region) were co-cultured with COS-A2-SSX-2 cells. Proliferation in terms of [$^3$H]-thymidine incorporation (CPM) was measured and is shown in FIGS. 6A (Donor 1) and 6B (Donor 2). These data show that PBLs transduced with SSX-2 TCR, codon-optimized SSX-2 TCR, or codon-optimized SSX-2 TCR including mouse constant region proliferate in response to co-culture with COS-A2-SSX-2 cells.

In another experiment, PBLs transduced as described in this example were co-cultured with 1300 mel cells, 624 mel cells, 888 mel cells, SK mel 37 cells, or COS-A2-SSX-2 cells. Proliferation in terms of [$^3$H]-thymidine incorporation counts per minute (CPM) was measured and is shown in FIGS. 9A-9E. These data show that PBLs transduced with SSX-2 TCR, codon-optimized SSX-2 TCR, or codon-optimized SSX-2 TCR including mouse constant region proliferate in response to co-culture with SSX2+/HLA-A2+ target cells.

Example 9

This example demonstrates that PBLs engineered with the SSX-2 TCR, codon-optimized SSX-2 TCR, or a codon-optimized human-mouse chimera SSX-2 TCR show specific lytic activity against SSX-2$^+$/HLA-A2$^+$ target cells.

PBLs that were untransduced (UT) or transduced with a vector comprising SEQ ID NO: 27 (SSX-2 TCR), SEQ ID NO: 29 (codon-optimized SSX-2 TCR), or SEQ ID NO: 30 (codon-optimized SSX-2 TCR including mouse constant region) were co-cultured with target cells 938 mel (HLA-A2−/SSX-2+), COS-A2, 938-A2 mel, COS-A2-SSX-2, 624 mel, 1300 mel, SK mel 37, or 888 mel at the effector to target ratios set forth in FIGS. 7A-D and 8A-D. Percent lysis of the target cells was measured and is shown in FIGS. 7A-D and 8A-D. Untransduced cells showed little to no reactivity. These data show that PBLs engineered with the SSX-2 TCR, codon-optimized SSX-2 TCR, or a codon-optimized human-mouse chimera SSX-2 TCR show specific lytic activity against SSX-2$^+$/HLA-A2$^+$ target cells.

Example 10

This example demonstrates that PBLs engineered with the SSX-2 TCR, codon-optimized SSX-2 TCR, or a codon-optimized human-mouse chimera SSX-2 TCR secrete cytokine when co-cultured with peptide-pulsed T2 cells.

Figure 10:
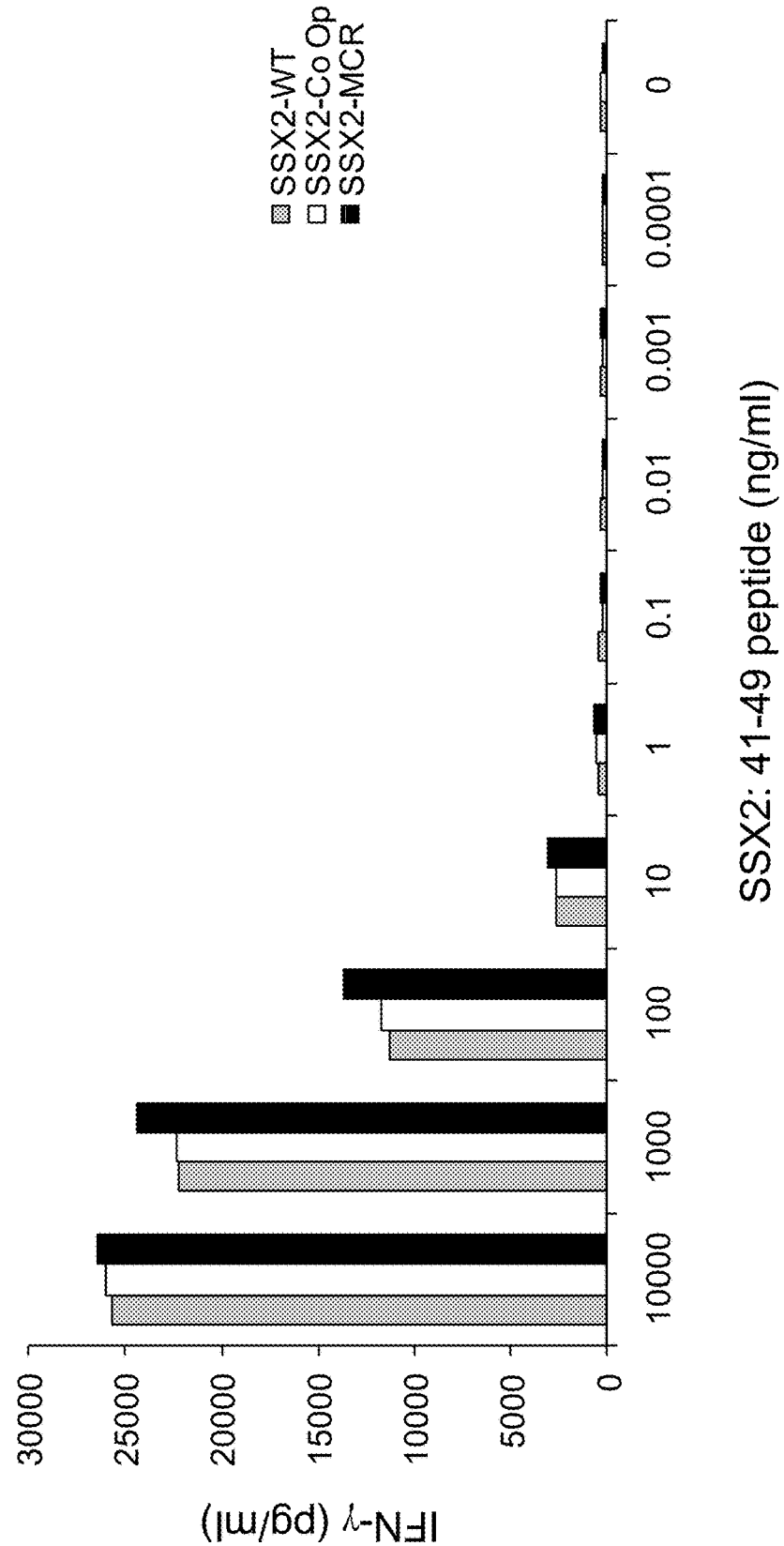
FIG. 10 is a bar graph showing IFN-γ levels measured after PBLs transduced with SSX-2 TCR ("SSX2-WT") (grey bars), codon-optimized SSX-2 TCR ("SSX2-Co Op") (unshaded bars), or a codon-optimized human-mouse chimera SSX-2 TCR ("SSX2-MCR") (black bars) were co-cultured with T2 cells from a human donor, wherein the T2 cells were pulsed with varying concentrations of the SSX-2: 41-49 peptide.

PBLs that were untransduced (UT) or transduced with a vector comprising SEQ ID NO: 27 (SSX-2 TCR), SEQ ID NO: 29 (codon-optimized SSX-2 TCR), or SEQ ID NO: 30 (codon-optimized SSX-2 TCR including mouse constant region) were co-cultured with T2 cells that were pulsed with an SSX-2 were pulsed with varying concentrations of the SSX-2: 41-49 (KASEKIFYV) (SEQ ID NO: 1) peptide. FIG. 10 shows the resulting interferon-γ levels (pg/ml) measured. These data show that SSX-2 TCR-transduced PBLs recognize SSX-2: 41-49 peptide.

Example 11

This example demonstrates that the demethylating agent, 5-aza-2'-deoxycytidine (DAC), enhances the recognition of mel1300 cells by SSX2-TCR engineered PBL.

Figure 12:
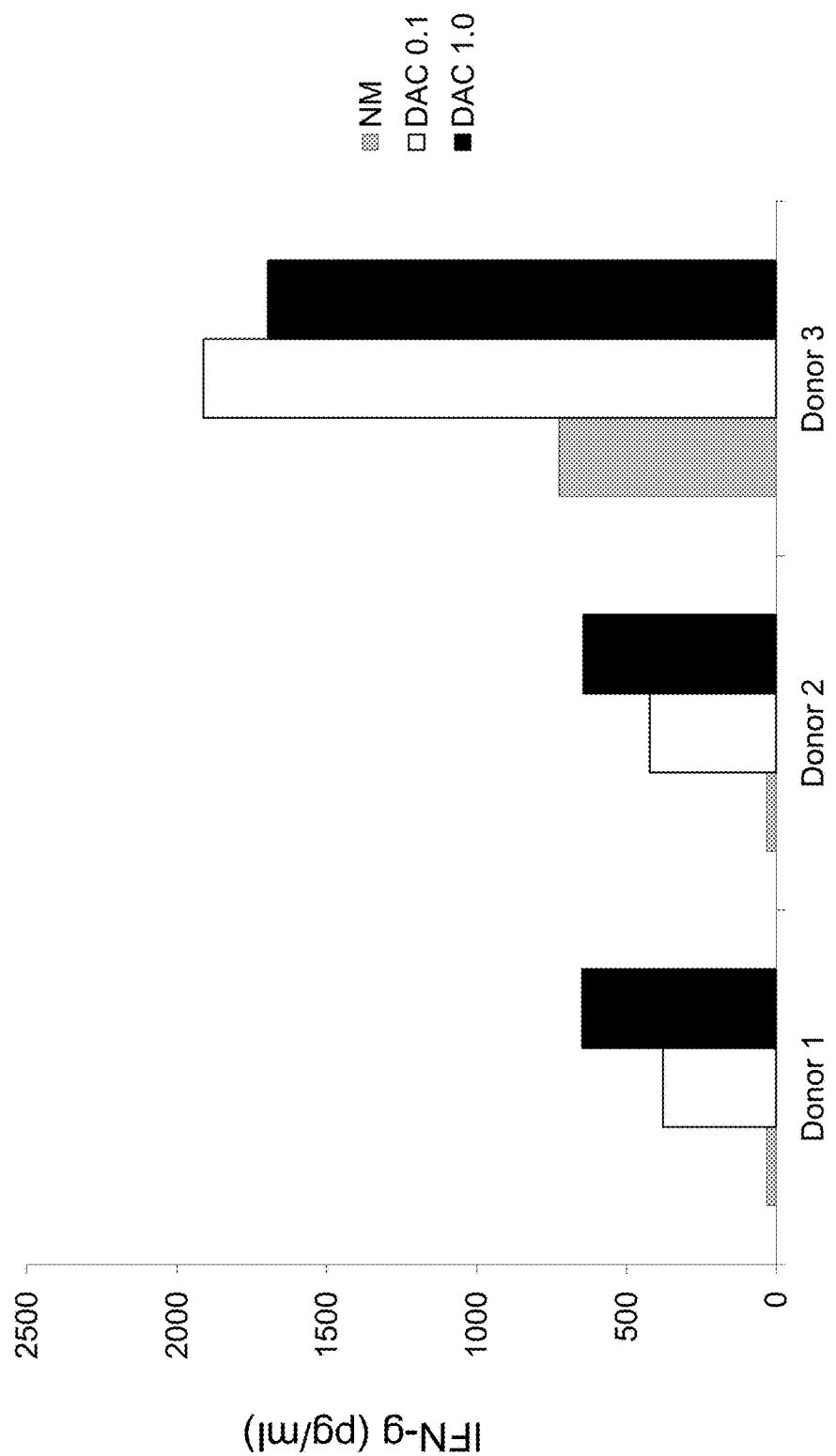
FIG. 12 is a bar graph that shows IFN-γ levels after PBLs from a human donor that were transduced with a SSX-2 TCR were co-cultured with mel1300 cells in the absence (grey bars) or in the presence (0.1 μM (unshaded bars) or 1.0 μM (black bars)) of the demethylating agent, 5-aza-2'-deoxycytidine (DAC). NM is normal media with no drug control.

SSX-2 TCR-transduced PBLs from three donors were co-cultured with mel1300 cells without DAC or with 0.1 μM or 1.0 μM DAC. FIG. 12 shows the resulting interferon-γ levels (pg/ml) measured. These data show that DAC enhances the recognition of mel1300 cells by SSX2-TCR engineered PBL.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified nucleic acid comprising a nucleotide sequence encoding a T cell receptor (TCR) having antigenic specificity for synovial sarcoma X Breakpoint (SSX)-2 (SEQ ID NO: 1), wherein the TCR comprises the amino acid sequences of SEQ ID NOs: 13-18.

2. The nucleic acid of claim 1, wherein the TCR also recognizes any one or more of SSX-3 (SEQ ID NO: 3), SSX-4 (SEQ ID NO: 4), SSX-5 (SEQ ID NO: 5), SSX-9 (SEQ ID NO: 6), and SSX-10 (SEQ ID NO: 7).

3. The nucleic acid of claim 1, wherein the TCR has antigenic specificity for an SSX-2 peptide comprising KASEKIFYV (SEQ ID NO: 2).

4. The nucleic acid of claim 1, wherein the TCR recognizes any one or more of KVSEKIVYV (SEQ ID NO: 8), KSSEKIVYV (SEQ ID NO: 9), KASEKIIYV (SEQ ID NO: 10), KSSEKIIYV (SEQ ID NO: 11), and KASEKILYV (SEQ ID NO: 12).

5. The nucleic acid of claim 1, wherein the TCR comprises SEQ ID NOs: 19 and 20.

6. The nucleic acid of claim 5, wherein the TCR further comprises SEQ ID NOs: 21 and 22.

7. The nucleic acid of claim 1, wherein the TCR comprises:
   a) SEQ ID NO: 23 and 24 or
   b) SEQ ID NO: 25 and 26.

8. An isolated or purified nucleic acid comprising a nucleotide sequence encoding a polypeptide comprising a functional portion of the TCR of claim 1, wherein the functional portion comprises the amino acid sequences of SEQ ID NOs: 13-18.

9. The isolated or purified nucleic acid of claim 8, wherein the portion comprises the amino acid sequences of SEQ ID NOs: 19 and 20.

10. The isolated or purified nucleic acid of claim 9, comprising:
    a) SEQ ID NO: 23 and 24; or
    b) SEQ ID NO: 25 and 26.

11. An isolated or purified nucleic acid encoding a protein, wherein the protein comprises a first polypeptide chain comprising the amino acid sequences of SEQ ID NOs: 13-15 and a second polypeptide chain comprising the amino acid sequences of SEQ ID NOs: 16-18.

12. The isolated or purified nucleic acid of claim 11, wherein the protein comprises a first polypeptide chain comprising SEQ ID NO: 19 and a second polypeptide chain comprising SEQ ID NO: 20.

13. The isolated or purified nucleic acid of claim 12, wherein the protein comprises:
    a) a first polypeptide chain comprising SEQ ID NO: 23 and a second polypeptide chain comprising SEQ ID NO: 24; or
    b) a first polypeptide chain comprising SEQ ID NO: 25 and a second polypeptide chain comprising SEQ ID NO: 26.

14. The isolated or purified nucleic acid of claim 11, wherein the protein is a fusion protein.

15. The isolated or purified nucleic acid of claim 11, wherein the protein is a recombinant antibody.

16. The nucleic acid of claim 1, wherein the nucleic acid comprises a nucleotide sequence comprising any one of SEQ ID NOs: 27-30.

17. A recombinant expression vector comprising the nucleic acid of claim 1.

18. The recombinant expression vector of claim 17, wherein the vector is a retroviral vector.

19. An isolated host cell comprising the recombinant expression vector of claim 17.

20. The isolated host cell of claim 19, wherein the cell is a peripheral blood lymphocyte (PBL).

21. The isolated host cell of claim 20, wherein the PBL is a CD8+ T cell or a CD4+ T cell.

22. A population of cells comprising at least one host cell of claim 19.

23. A pharmaceutical composition comprising the host cell of claim 19, and a pharmaceutically acceptable carrier.

* * * * *

SEQUENCE LISTING

```
<160> NUMBER OF SEQ ID NOS: 38

<210> SEQ ID NO 1
<211> LENGTH: 223
<212> TYPE: PRT
<213> ORGANISM: Homo sapiens

<400> SEQUENCE: 1

Met Asn Gly Asp Asp Ala Phe Ala Arg Arg Pro Thr Val Gly Ala Gln
1               5                   10                  15

Ile Pro Glu Lys Ile Gln Lys Ala Phe Asp Asp Ile Ala Lys Tyr Phe
            20                  25                  30

Ser Lys Glu Glu Trp Glu Lys Met Lys Ala Ser Glu Lys Ile Phe Tyr
        35                  40                  45
```

```
Val Tyr Met Lys Arg Lys Tyr Glu Ala Met Thr Lys Leu Gly Phe Lys
 50                  55                  60

Ala Thr Leu Pro Pro Phe Met Cys Asn Lys Arg Ala Glu Asp Phe Gln
 65                  70                  75                  80

Gly Asn Asp Leu Asp Asn Asp Pro Asn Arg Gly Asn Gln Val Glu Arg
                 85                  90                  95

Pro Gln Met Thr Phe Gly Arg Leu Gln Gly Ile Ser Pro Lys Ile Met
                100                 105                 110

Pro Lys Lys Pro Ala Glu Glu Gly Asn Asp Ser Glu Val Pro Glu
                115                 120                 125

Ala Ser Gly Pro Gln Asn Asp Gly Lys Glu Leu Cys Pro Pro Gly Lys
            130                 135                 140

Pro Thr Thr Ser Glu Lys Ile His Glu Arg Ser Gly Asn Arg Glu Ala
145                 150                 155                 160

Gln Glu Lys Glu Arg Arg Gly Thr Ala His Arg Trp Ser Ser Gln
                165                 170                 175

Asn Thr His Asn Ile Gly Arg Phe Ser Leu Ser Thr Ser Met Gly Ala
            180                 185                 190

Val His Gly Thr Pro Lys Thr Ile Thr His Asn Arg Asp Pro Lys Gly
        195                 200                 205

Gly Asn Met Pro Gly Pro Thr Asp Cys Val Arg Glu Asn Ser Trp
    210                 215                 220

<210> SEQ ID NO 2
<211> LENGTH: 9
<212> TYPE: PRT
<213> ORGANISM: Homo sapiens

<400> SEQUENCE: 2

Lys Ala Ser Glu Lys Ile Phe Tyr Val
 1               5

<210> SEQ ID NO 3
<211> LENGTH: 188
<212> TYPE: PRT
<213> ORGANISM: Homo sapiens

<400> SEQUENCE: 3

Met Asn Gly Asp Asp Thr Phe Ala Arg Arg Pro Thr Val Gly Ala Gln
 1               5                  10                  15

Ile Pro Glu Lys Ile Gln Lys Ala Phe Asp Asp Ile Ala Lys Tyr Phe
                 20                  25                  30

Ser Lys Glu Glu Trp Glu Lys Met Lys Val Ser Glu Lys Ile Val Tyr
             35                  40                  45

Val Tyr Met Lys Arg Lys Tyr Glu Ala Met Thr Lys Leu Gly Phe Lys
 50                  55                  60

Ala Ile Leu Pro Ser Phe Met Arg Asn Lys Arg Val Thr Asp Phe Gln
 65                  70                  75                  80

Gly Asn Asp Phe Asp Asn Asp Pro Asn Arg Gly Asn Gln Val Gln Arg
                 85                  90                  95

Pro Gln Met Thr Phe Gly Arg Leu Gln Gly Ile Phe Pro Lys Ile Met
                100                 105                 110

Pro Lys Lys Pro Ala Glu Glu Gly Asn Val Ser Lys Glu Val Pro Glu
                115                 120                 125

Ala Ser Gly Pro Gln Asn Asp Gly Lys Gln Leu Cys Pro Pro Gly Lys
            130                 135                 140
```

```
Pro Thr Thr Ser Glu Lys Ile Asn Met Ile Ser Gly Pro Lys Arg Gly
145                 150                 155                 160

Glu His Ala Trp Thr His Arg Leu Arg Glu Arg Lys Gln Leu Val Ile
                165                 170                 175

Tyr Glu Glu Ile Ser Asp Pro Glu Glu Asp Glu
            180                 185

<210> SEQ ID NO 4
<211> LENGTH: 188
<212> TYPE: PRT
<213> ORGANISM: Homo sapiens

<400> SEQUENCE: 4

Met Asn Gly Asp Asp Ala Phe Ala Arg Arg Pro Arg Asp Asp Ala Gln
1               5                   10                  15

Ile Ser Glu Lys Leu Arg Lys Ala Phe Asp Asp Ile Ala Lys Tyr Phe
            20                  25                  30

Ser Lys Lys Glu Trp Glu Lys Met Lys Ser Ser Glu Lys Ile Val Tyr
        35                  40                  45

Val Tyr Met Lys Leu Asn Tyr Glu Val Met Thr Lys Leu Gly Phe Lys
50                  55                  60

Val Thr Leu Pro Pro Phe Met Arg Ser Lys Arg Ala Ala Asp Phe His
65                  70                  75                  80

Gly Asn Asp Phe Gly Asn Asp Arg Asn His Arg Asn Gln Val Glu Arg
                85                  90                  95

Pro Gln Met Thr Phe Gly Ser Leu Gln Arg Ile Phe Pro Lys Ile Met
            100                 105                 110

Pro Lys Lys Pro Ala Glu Glu Asn Gly Leu Lys Glu Val Pro Glu
        115                 120                 125

Ala Ser Gly Pro Gln Asn Asp Gly Lys Gln Leu Cys Pro Pro Gly Asn
    130                 135                 140

Pro Ser Thr Leu Glu Lys Ile Asn Lys Thr Ser Gly Pro Lys Arg Gly
145                 150                 155                 160

Lys His Ala Trp Thr His Arg Leu Arg Glu Arg Lys Gln Leu Val Val
                165                 170                 175

Tyr Glu Glu Ile Ser Asp Pro Glu Glu Asp Glu
            180                 185

<210> SEQ ID NO 5
<211> LENGTH: 229
<212> TYPE: PRT
<213> ORGANISM: Homo sapiens

<400> SEQUENCE: 5

Met Asn Gly Asp Asp Ala Phe Val Arg Arg Pro Arg Val Gly Ser Gln
1               5                   10                  15

Ile Pro Gln Lys Met Gln Lys His Pro Trp Arg Gln Val Cys Asp Arg
            20                  25                  30

Gly Ile His Leu Val Asn Leu Ser Pro Phe Trp Lys Val Gly Arg Glu
        35                  40                  45

Pro Ala Ser Ser Ile Lys Ala Leu Leu Cys Gly Arg Gly Glu Ala Arg
50                  55                  60

Ala Phe Asp Asp Ile Ala Lys Tyr Phe Ser Lys Glu Trp Glu Lys
65                  70                  75                  80

Met Lys Ala Ser Glu Lys Ile Ile Tyr Val Tyr Met Lys Arg Lys Tyr
                85                  90                  95
```

```
Glu Ala Met Thr Lys Leu Gly Phe Lys Ala Thr Leu Pro Pro Phe Met
            100                 105                 110

Arg Asn Lys Arg Val Ala Asp Phe Gln Gly Asn Asp Phe Asp Asn Asp
        115                 120                 125

Pro Asn Arg Gly Asn Gln Val Glu His Pro Gln Met Thr Phe Gly Arg
    130                 135                 140

Leu Gln Gly Ile Phe Pro Lys Ile Thr Pro Glu Lys Pro Ala Glu Glu
145                 150                 155                 160

Gly Asn Asp Ser Lys Gly Val Pro Glu Ala Ser Gly Pro Gln Asn Asn
                165                 170                 175

Gly Lys Gln Leu Arg Pro Ser Gly Lys Leu Asn Thr Ser Glu Lys Val
            180                 185                 190

Asn Lys Thr Ser Gly Pro Lys Arg Gly Lys His Ala Trp Thr His Arg
        195                 200                 205

Val Arg Glu Arg Lys Gln Leu Val Ile Tyr Glu Glu Ile Ser Asp Pro
    210                 215                 220

Gln Glu Asp Asp Glu
225

<210> SEQ ID NO 6
<211> LENGTH: 188
<212> TYPE: PRT
<213> ORGANISM: Homo sapiens

<400> SEQUENCE: 6

Met Asn Gly Asp Asp Ala Phe Ala Arg Arg Pro Arg Ala Gly Ser Gln
1               5                   10                  15

Ile Pro Glu Lys Ile Gln Lys Ala Phe Asp Asp Ile Ala Lys Tyr Phe
            20                  25                  30

Ser Lys Lys Glu Trp Glu Lys Met Lys Ser Ser Glu Lys Ile Ile Tyr
        35                  40                  45

Val Tyr Met Lys Arg Lys Tyr Glu Ala Met Thr Lys Leu Gly Phe Lys
    50                  55                  60

Ala Thr Leu Pro Pro Phe Met Cys Asn Thr Gly Ala Thr Asp Leu Gln
65                  70                  75                  80

Gly Asn Asp Phe Asp Asn Asp Arg Asn His Arg Asn Gln Val Glu Arg
                85                  90                  95

Ser Gln Met Thr Phe Gly Arg Leu Gln Gly Ile Phe Pro Lys Ile Met
            100                 105                 110

Pro Lys Lys Pro Ala Glu Val Gly Asn Asp Ser Lys Glu Val Pro Glu
        115                 120                 125

Ala Ser Gly Leu Gln Asn Asp Gly Lys Gln Leu Cys Pro Pro Gly Lys
    130                 135                 140

Pro Thr Thr Ser Glu Lys Ile Asn Lys Ala Ser Gly Pro Lys Arg Gly
145                 150                 155                 160

Lys His Ala Trp Thr His Arg Leu Arg Glu Arg Lys Gln Leu Val Ile
                165                 170                 175

Tyr Glu Glu Ile Ser Asp Pro Glu Glu Asp Asp Glu
            180                 185

<210> SEQ ID NO 7
<211> LENGTH: 151
<212> TYPE: PRT
<213> ORGANISM: Homo sapiens

<400> SEQUENCE: 7
```

-continued

```
Met Asn Gly Asp Asp Ala Phe Ala Arg Arg Pro Arg Val Asp Ala Gln
1               5                   10                  15

Ile Pro Glu Lys Ile Gln Lys Ala Phe Asp Asp Ile Ala Lys Tyr Phe
            20                  25                  30

Ser Lys Glu Glu Trp Glu Lys Met Lys Ala Ser Glu Lys Ile Leu Tyr
        35                  40                  45

Val Tyr Met Lys Arg Lys Tyr Glu Ala Met Thr Lys Leu Gly Phe Lys
    50                  55                  60

Ala Thr Leu Pro Pro Phe Met Cys Asn Lys Arg Thr Ala Asp Phe Gln
65                  70                  75                  80

Gly Asn Asp Phe Asp Asn Asp Tyr Asn His Gly His Gln Gly Ser Thr
                85                  90                  95

Val His Ala Ser Ser Ser Phe Leu His Val Pro Gln Met Thr Ile Ser
            100                 105                 110

Ser Val Ser Leu Pro Thr Tyr Ser Gln Met Asp His Pro Ser Pro Arg
            115                 120                 125

Thr Arg Lys Leu Phe Arg Glu Arg Arg Pro Asn Cys Pro Thr Thr Cys
    130                 135                 140

Cys Arg Ile Leu Leu Gln Asp
145                 150

<210> SEQ ID NO 8
<211> LENGTH: 9
<212> TYPE: PRT
<213> ORGANISM: Homo sapiens

<400> SEQUENCE: 8

Lys Val Ser Glu Lys Ile Val Tyr Val
1               5

<210> SEQ ID NO 9
<211> LENGTH: 9
<212> TYPE: PRT
<213> ORGANISM: Homo sapiens

<400> SEQUENCE: 9

Lys Ser Ser Glu Lys Ile Val Tyr Val
1               5

<210> SEQ ID NO 10
<211> LENGTH: 9
<212> TYPE: PRT
<213> ORGANISM: Homo sapiens

<400> SEQUENCE: 10

Lys Ala Ser Glu Lys Ile Ile Tyr Val
1               5

<210> SEQ ID NO 11
<211> LENGTH: 9
<212> TYPE: PRT
<213> ORGANISM: Homo sapiens

<400> SEQUENCE: 11

Lys Ser Ser Glu Lys Ile Ile Tyr Val
1               5

<210> SEQ ID NO 12
<211> LENGTH: 9
<212> TYPE: PRT
<213> ORGANISM: Homo sapiens
```

<400> SEQUENCE: 12

Lys Ala Ser Glu Lys Ile Leu Tyr Val
1               5

<210> SEQ ID NO 13
<211> LENGTH: 7
<212> TYPE: PRT
<213> ORGANISM: Homo sapiens

<400> SEQUENCE: 13

Thr Ser Asp Pro Ser Tyr Gly
1               5

<210> SEQ ID NO 14
<211> LENGTH: 4
<212> TYPE: PRT
<213> ORGANISM: Homo sapiens

<400> SEQUENCE: 14

Gln Gly Ser Tyr
1

<210> SEQ ID NO 15
<211> LENGTH: 14
<212> TYPE: PRT
<213> ORGANISM: Homo sapiens

<400> SEQUENCE: 15

Cys Ala Met Thr Ser Gly Phe Gly Asn Glu Lys Leu Thr Phe
1               5                   10

<210> SEQ ID NO 16
<211> LENGTH: 5
<212> TYPE: PRT
<213> ORGANISM: Homo sapiens

<400> SEQUENCE: 16

Leu Asn His Asn Val
1               5

<210> SEQ ID NO 17
<211> LENGTH: 6
<212> TYPE: PRT
<213> ORGANISM: Homo sapiens

<400> SEQUENCE: 17

Tyr Tyr Asp Lys Asp Phe
1               5

<210> SEQ ID NO 18
<211> LENGTH: 14
<212> TYPE: PRT
<213> ORGANISM: Homo sapiens

<400> SEQUENCE: 18

Cys Ala Thr Ser Arg Gly Gln Gly Gly Gln Pro Gln His Phe
1               5                   10

<210> SEQ ID NO 19
<211> LENGTH: 115
<212> TYPE: PRT
<213> ORGANISM: Homo sapiens

<400> SEQUENCE: 19

```
Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Pro Ser Tyr
            20                  25                  30

Gly Leu Phe Trp Tyr Lys Gln Pro Ser Ser Glu Met Ile Phe Leu
                35                  40                  45

Ile Tyr Gln Gly Ser Tyr Asp Gln Gln Asn Ala Thr Glu Gly Arg Tyr
50                      55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys Ala Met Thr Ser
                85                  90                  95

Gly Phe Gly Asn Glu Lys Leu Thr Phe Gly Thr Gly Thr Arg Leu Thr
                100                 105                 110

Ile Ile Pro
        115

<210> SEQ ID NO 20
<211> LENGTH: 114
<212> TYPE: PRT
<213> ORGANISM: Homo sapiens

<400> SEQUENCE: 20

Asp Ala Met Val Ile Gln Asn Pro Arg Tyr Gln Val Thr Gln Phe Gly
1               5                   10                  15

Lys Pro Val Thr Leu Ser Cys Ser Gln Thr Leu Asn His Asn Val Met
            20                  25                  30

Tyr Trp Tyr Gln Gln Lys Ser Ser Gln Ala Pro Lys Leu Leu Phe His
                35                  40                  45

Tyr Tyr Asp Lys Asp Phe Asn Asn Glu Ala Asp Thr Pro Asp Asn Phe
50                      55                  60

Gln Ser Arg Arg Pro Asn Thr Ser Phe Cys Phe Leu Asp Ile Arg Ser
65                  70                  75                  80

Pro Gly Leu Gly Asp Ala Ala Met Tyr Leu Cys Ala Thr Ser Arg Gly
                85                  90                  95

Gln Gly Gly Gln Pro Gln His Phe Gly Asp Gly Thr Arg Leu Ser Ile
                100                 105                 110

Leu Glu

<210> SEQ ID NO 21
<211> LENGTH: 137
<212> TYPE: PRT
<213> ORGANISM: Mus musculus

<400> SEQUENCE: 21

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Thr
            35                  40                  45

Val Leu Asp Met Lys Ala Met Asp Ser Lys Ser Asn Gly Ala Ile Ala
50                      55                  60

Trp Ser Asn Gln Thr Ser Phe Thr Cys Gln Asp Ile Phe Lys Glu Thr
65                  70                  75                  80
```

```
Asn Ala Thr Tyr Pro Ser Ser Asp Val Pro Cys Asp Ala Thr Leu Thr
                 85                  90                  95

Glu Lys Ser Phe Glu Thr Asp Met Asn Leu Asn Phe Gln Asn Leu Ser
            100                 105                 110

Val Met Gly Leu Arg Ile Leu Leu Lys Val Ala Gly Phe Asn Leu
        115                 120                 125

Leu Met Thr Leu Arg Leu Trp Ser Ser
    130                 135

<210> SEQ ID NO 22
<211> LENGTH: 170
<212> TYPE: PRT
<213> ORGANISM: Mus musculus

<400> SEQUENCE: 22

Asp Leu Arg Asn Val Thr Pro Pro Lys Val Ser Leu Phe Glu Pro Ser
1               5                   10                  15

Lys Ala Glu Ile Ala Asn Lys Gln Lys Ala Thr Leu Val Cys Leu Ala
            20                  25                  30

Arg Gly Phe Phe Pro Asp His Val Glu Leu Ser Trp Trp Val Asn Gly
        35                  40                  45

Lys Glu Val His Ser Gly Val Ser Thr Asp Pro Gln Ala Tyr Lys Glu
    50                  55                  60

Ser Asn Tyr Ser Tyr Cys Leu Ser Ser Arg Leu Arg Val Ser Ala Thr
65                  70                  75                  80

Phe Trp His Asn Pro Arg Asn His Phe Arg Cys Gln Val Gln Phe His
                85                  90                  95

Gly Leu Ser Glu Glu Asp Lys Trp Pro Glu Gly Ser Pro Lys Pro Val
            100                 105                 110

Thr Gln Asn Ile Ser Ala Glu Ala Trp Gly Arg Ala Cys Gly Ile Thr
        115                 120                 125

Ser Ser Tyr Gln Gln Gly Val Leu Ser Ala Thr Ile Leu Tyr Glu Ile
    130                 135                 140

Leu Leu Gly Lys Ala Thr Leu Tyr Ala Val Leu Val Ser Thr Leu Val
145                 150                 155                 160

Val Met Ala Met Val Lys Arg Lys Asn Ser
                165                 170

<210> SEQ ID NO 23
<211> LENGTH: 276
<212> TYPE: PRT
<213> ORGANISM: Homo sapiens

<400> SEQUENCE: 23

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Asn Ala Thr
65                  70                  75                  80

Glu Gly Arg Tyr Ser Leu Asn Phe Gln Lys Ala Arg Lys Ser Ala Asn
                85                  90                  95
```

```
Leu Val Ile Ser Ala Ser Gln Leu Gly Asp Ser Ala Met Tyr Phe Cys
            100                 105                 110

Ala Met Thr Ser Gly Phe Gly Asn Glu Lys Leu Thr Phe Gly Thr Gly
            115                 120                 125

Thr Arg Leu Thr Ile Ile Pro Asn Ile Gln Asn Pro Asp Pro Ala Val
130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
            195                 200                 205

Ala Asn Ala Phe Asn Asn Ser Ile Ile Pro Glu Asp Thr Phe Phe Pro
            210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
            275

<210> SEQ ID NO 24
<211> LENGTH: 309
<212> TYPE: PRT
<213> ORGANISM: Homo sapiens

<400> SEQUENCE: 24

Met Gly Pro Gly Leu Leu His Trp Met Ala Leu Cys Leu Leu Gly Thr
1               5                   10                  15

Gly His Gly Asp Ala Met Val Ile Gln Asn Pro Arg Tyr Gln Val Thr
            20                  25                  30

Gln Phe Gly Lys Pro Val Thr Leu Ser Cys Ser Gln Thr Leu Asn His
        35                  40                  45

Asn Val Met Tyr Trp Tyr Gln Gln Lys Ser Ser Gln Ala Pro Lys Leu
    50                  55                  60

Leu Phe His Tyr Tyr Asp Lys Asp Phe Asn Asn Glu Ala Asp Thr Pro
65                  70                  75                  80

Asp Asn Phe Gln Ser Arg Arg Pro Asn Thr Ser Phe Cys Phe Leu Asp
                85                  90                  95

Ile Arg Ser Pro Gly Leu Gly Asp Ala Ala Met Tyr Leu Cys Ala Thr
            100                 105                 110

Ser Arg Gly Gln Gly Gly Gln Pro Gln His Phe Gly Asp Gly Thr Arg
            115                 120                 125

Leu Ser Ile Leu Glu Asp Leu Asn Lys Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190
```

```
Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
                260                 265                 270

Gly Val Leu Ser Ala Thr Ile Leu Tyr Glu Ile Leu Leu Gly Lys Ala
                275                 280                 285

Thr Leu Tyr Ala Val Leu Val Ser Ala Leu Val Leu Met Ala Met Val
        290                 295                 300

Lys Arg Lys Asp Phe
305

<210> SEQ ID NO 25
<211> LENGTH: 273
<212> TYPE: PRT
<213> ORGANISM: Artificial Sequence
<220> FEATURE:
<223> OTHER INFORMATION: Synthetic Polypeptide

<400> SEQUENCE: 25

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Thr Ser Gly Phe Gly Asn Glu Lys Leu Thr Phe Gly Thr Gly
        115                 120                 125

Thr Arg Leu Thr Ile Ile Pro Asn Asp Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Thr Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240
```

```
Asn Leu Asn Phe Gln Asn Leu Ser Val Met Gly Leu Arg Ile Leu Leu
                245                 250                 255

Leu Lys Val Ala Gly Phe Asn Leu Leu Met Thr Leu Arg Leu Trp Ser
        260                 265                 270

Ser

<210> SEQ ID NO 26
<211> LENGTH: 303
<212> TYPE: PRT
<213> ORGANISM: Artificial Sequence
<220> FEATURE:
<223> OTHER INFORMATION: Synthetic Polypeptide

<400> SEQUENCE: 26

Met Gly Pro Gly Leu Leu His Trp Met Ala Leu Cys Leu Leu Gly Thr
1               5                   10                  15

Gly His Gly Asp Ala Met Val Ile Gln Asn Pro Arg Tyr Gln Val Thr
            20                  25                  30

Gln Phe Gly Lys Pro Val Thr Leu Ser Cys Ser Gln Thr Leu Asn His
        35                  40                  45

Asn Val Met Tyr Trp Tyr Gln Gln Lys Ser Ser Gln Ala Pro Lys Leu
    50                  55                  60

Leu Phe His Tyr Tyr Asp Lys Asp Phe Asn Asn Glu Ala Asp Thr Pro
65                  70                  75                  80

Asp Asn Phe Gln Ser Arg Arg Pro Asn Thr Ser Phe Cys Phe Leu Asp
                85                  90                  95

Ile Arg Ser Pro Gly Leu Gly Asp Ala Ala Met Tyr Leu Cys Ala Thr
            100                 105                 110

Ser Arg Gly Gln Gly Gly Gln Pro Gln His Phe Gly Asp Gly Thr Arg
        115                 120                 125

Leu Ser Ile Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Cys Gly Ile Thr Ser Ser Tyr Gln Gln Gly Val Leu Ser Ala Thr
            260                 265                 270

Ile Leu Tyr Glu Ile Leu Leu Gly Lys Ala Thr Leu Tyr Ala Val Leu
        275                 280                 285

Val Ser Thr Leu Val Val Met Ala Met Val Lys Arg Lys Asn Ser
    290                 295                 300

<210> SEQ ID NO 27
<211> LENGTH: 1842
```

<212> TYPE: DNA
<213> ORGANISM: Artificial Sequence
<220> FEATURE:
<223> OTHER INFORMATION: Synthetic Polynucleotide

<400> SEQUENCE: 27

```
atgtcacttt ctagcctgct gaaggtggtc acagcttcac tgtggctagg acctggcatt      60
gcccagaaga taactcaaac ccaaccagga atgttcgtgc aggaaaagga ggctgtgact     120
ctggactgca catatgacac cagtgatcca agttatggtc tattctggta caagcagccc     180
agcagtgggg aaatgatttt tcttatttat caggggtctt atgaccagca aaatgcaaca     240
gaaggtcgct actcattgaa tttccagaag gcaagaaaat ccgccaacct tgtcatctcc     300
gcttcacaac tgggggactc agcaatgtac ttctgtgcaa tgaccagcgg gtttggaaat     360
gagaaattaa cctttgggac tggaacaaga ctcaccatca tacccaatat ccagaaccct     420
gaccctgccg tgtaccagct gagagactct aaatccagtg acaagtctgt ctgcctattc     480
accgattttg attctcaaac aaatgtgtca caaagtaagg attctgatgt gtatatcaca     540
gacaaaactg tgctagacat gaggtctatg gacttcaaga gcaacagtgc tgtggcctgg     600
agcaacaaat ctgactttgc atgtgcaaac gccttcaaca cagcattat tccagaagac     660
accttcttcc ccagcccaga aagttcctgt gatgtcaagc tggtcgagaa aagctttgaa     720
acagatacga acctaaactt tcaaaacctg tcagtgattg gttccgaat cctcctcctg     780
aaagtggccg ggtttaatct gctcatgacg ctgcggctgt ggtccagccg gccaagcgg     840
tccggatccg gagccaccaa cttcagcctg ctgaagcagg cgggcgacgt ggaggagaac     900
cccggcccca tgggtcctgg gcttctccac tggatggccc tttgtctcct tggaacaggt     960
catgggatg ccatggtcat ccagaaccca agataccagg ttacccagtt tggaaagcca    1020
gtgaccctga gttgttctca gactttgaac cataacgtca tgtactggta ccagcagaag    1080
tcaagtcagg ccccaaagct gctgttccac tactatgaca agattttaa caatgaagca    1140
gacaccctg ataacttcca atccaggagg ccgaacactt ctttctgctt tcttgacatc    1200
cgctcaccag gcctgggga cgcagccatg tacctgtgtg ccaccagcag aggacagggt    1260
gggcagcccc agcattttgg tgatgggact cgactctcca tcctagagga cctgaacaag    1320
gtgttcccac ccgaggtcgc tgtgtttgag ccatcagaag cagagatctc ccacacccaa    1380
aaggccacac tggtgtgcct ggccacaggc ttcttccctg accacgtgga gctgagctgg    1440
tgggtgaatg ggaaggaggt gcacagtggg gtcagcacgg accgcagcc cctcaaggag    1500
cagcccgccc tcaatgactc cagatactgc ctgagcagcc gctgagggt ctcggccacc    1560
ttctggcaga accccgcaa ccacttccgc tgtcaagtcc agttctacgg gctctcggag    1620
aatgacgagt ggacccagga tagggccaaa cccgtcaccc cgatcgtcag cgccgaggcc    1680
tggggtagag cagactgtgg ctttacctcg gtgtcctacc agcaaggggt cctgtctgcc    1740
accatcctct atgagatcct gctagggaag gccaccctgt atgctgtgct ggtcagcgcc    1800
cttgtgttga tggccatggt caagagaaag gatttctgat aa                      1842
```

<210> SEQ ID NO 28
<211> LENGTH: 1815
<212> TYPE: DNA
<213> ORGANISM: Artificial Sequence
<220> FEATURE:
<223> OTHER INFORMATION: Synthetic Polynucleotide

<400> SEQUENCE: 28

| | |
|---|---|
| atgtcacttt ctagcctgct gaaggtggtc acagcttcac tgtggctagg acctggcatt | 60 |
| gcccagaaga taactcaaac ccaaccagga atgttcgtgc aggaaaagga ggctgtgact | 120 |
| ctggactgca catatgacac cagtgatcca agttatggtc tattctggta caagcagccc | 180 |
| agcagtgggg aaatgatttt tcttatttat caggggtctt atgaccagca aaatgcaaca | 240 |
| gaaggtcgct actcattgaa tttccagaag gcaagaaaat ccgccaacct tgtcatctcc | 300 |
| gcttcacaac tgggggactc agcaatgtac ttctgtgcaa tgaccagcgg gtttggaaat | 360 |
| gagaaattaa cctttgggac tggaacaaga ctcaccatca tacccaatga catccagaac | 420 |
| ccagaacctg ctgtgtacca gttaaaagat cctcggtctc aggacagcac cctctgcctg | 480 |
| ttcaccgact ttgactccca aatcaatgtg ccgaaaacca tggaatctgg aacgttcatc | 540 |
| actgacaaaa ctgtgctgga catgaaagct atggattcca agagcaatgg ggccattgcc | 600 |
| tggagcaacc agacaagctt cacctgccaa gatatcttca aagagaccaa cgccacctac | 660 |
| cccagttcag acgttccctg tgatgccacg ttgactgaga aaagctttga acagatatg | 720 |
| aacctaaact ttcaaaacct gtcagttatg ggactccgaa tcctcctgct gaaagtagcc | 780 |
| ggatttaacc tgctcatgac gctgaggctg tggtccagtc gggccaagcg gtccggatcc | 840 |
| ggagccacca cttcagcct gctgaagcag gcgggcgacg tggaggagaa ccccggcccc | 900 |
| atgggtcctg ggcttctcca ctggatggcc ctttgtctcc ttggaacagg tcatggggat | 960 |
| gccatggtca tccagaaccc aagataccag gttacccagt ttggaaagcc agtgaccctg | 1020 |
| agttgttctc agactttgaa ccataacgtc atgtactggt accagcagaa gtcaagtcag | 1080 |
| gcccccaaagc tgctgttcca ctactatgac aaagatttta acaatgaagc agacaccct | 1140 |
| gataacttcc aatccaggag gccgaacact tctttctgct tcttgacat ccgctcacca | 1200 |
| ggcctggggg acgcagccat gtacctgtgt gccaccagca gggacagg gtgggcagccc | 1260 |
| cagcattttg gtgatgggac tcgactctcc atcctagagg atctgagaaa tgtgactcca | 1320 |
| cccaaggtct ccttgtttga gccatcaaaa gcagagattg caaacaaaca aaaggctacc | 1380 |
| ctcgtgtgct tggccagggg cttcttccct gaccacgtgg agctgagctg gtgggtgaat | 1440 |
| ggcaaggagg tccacagtgg ggtcagcacg gaccctcagg cctacaagga gagcaattat | 1500 |
| agctactgcc tgagcagccg cctgagggtc tctgctacct tctggcacaa tcctcgcaac | 1560 |
| cacttccgct gccaagtgca gttccatggg ctttcagagg aggacaagtg gccagagggc | 1620 |
| tcacccaaac ctgtcacaca gaacatcagt gcagaggcct ggggccgagc atgtgggatt | 1680 |
| acctcatcct atcaacaagg ggtcttgtct gccaccatcc tctatgagat cctgctaggg | 1740 |
| aaagccaccc tgtatgctgt gcttgtcagt acactggtgg tgatggctat ggtcaaaaga | 1800 |
| aagaactcat gataa | 1815 |

<210> SEQ ID NO 29
<211> LENGTH: 1842
<212> TYPE: DNA
<213> ORGANISM: Artificial Sequence
<220> FEATURE:
<223> OTHER INFORMATION: Synthetic Polynucleotide

<400> SEQUENCE: 29

| | |
|---|---|
| atggcactga gcagcctgct gaaggtggtg acagccagcc tgtggctggg ccctggaatc | 60 |
| gcccagaaga tcacccagac ccagcccggc atgttcgtgc aggaaaaga gccgtgacc | 120 |
| ctggactgca cctacgacac cagcgacccc agctacggc tgttctggta caagcagccc | 180 |
| agcagcggcg agatgatctt cctgatctac caggcagct acgaccagca gaacgccacc | 240 |

```
gagggccggt acagcctcaa cttccagaag gcccggaagt ccgccaacct ggtgatcagc    300
gccagccagc tgggcgacag cgccatgtac ttttgcgcca tgaccagcgg cttcggcaac    360
gagaagctga ccttcggcac cggcacccgg ctgaccatca tccccaacat ccagaacccc    420
gatcctgctg tgtaccagct gagggacagc aagagcagcg acaagagcgt gtgcctgttc    480
accgacttcg acagccagac caacgtgtct cagtctaagg atagtgatgt gtatatcacc    540
gacaagaccg tgctggacat gcggagcatg gacttcaaga gcaacagcgc cgtggcctgg    600
tccaacaaga gcgacttcgc ctgcgccaac gccttcaaca acagcatcat ccccgaggac    660
acctttttcc ccagcccgga gagcagctgc gacgtgaaac tggtggagaa gagcttcgag    720
acagacacca acctgaactt ccagaacctg agcgtgatcg gcttcagaat cctgctgctg    780
aaggtggccg gcttcaacct gctgatgacc ctgcggctgt ggagcagccg ggccaagaga    840
agcggcagcg gcgccaccaa cttcagcctg ctgaagcagg ccggcgacgt ggaggaaaac    900
cctggcccta tgggacctgg cctgctgcac tggatggccc tgtgtctgct gggcacaggc    960
cacggcgacg ctatggtgat ccagaatccc agataccagg tgacacagtt cggcaagccc   1020
gtgacactga gctgcagcca gacccctgaac cacaacgtga tgtactggta tcagcagaag   1080
tccagccagg cccccaagct gctgttccac tactacgaca aggacttcaa caacgaggcc   1140
gacacccccg acaacttcca gagcagacgg cccaatacca gcttctgctt cctggacatc   1200
agaagccctg gcctggggga cgccgccatg tacctgtgtg ccaccagcag aggccagggc   1260
ggacagcccc agcacttcgg cgacggcacc agactgagca tcctcgagga cctgaacaag   1320
gtgttccccc ccgaggtggc cgtgttcgag cccagcgagg ccgagattag ccacacccag   1380
aaagccaccc tggtgtgcct ggccaccggc ttttttcccg accacgtgga gctgtcttgg   1440
tgggtgaacg gcaaagaggt gcacagcggg gtctccaccg accccagcc cctgaaagag   1500 cagcccgccc tgaacgacag ccggtactgc ctctcttctc ggctgagagt gtccgccacc   1560
ttctggcaga accccggaa ccacttccgg tgccaggtgc agttctacgg cctgagcgag   1620
aacgacgagt ggaccccagga cagagccaag cctgtgaccc agatcgtgtc tgccgaggcc   1680
tgggggcgcg ccgattgcgg cttcaccagc gtgtcctacc agcagggcgt gctgtctgcc   1740
accatcctgt acgagatcct gctgggcaag gccaccctgt acgccgtgct ggtgtccgcc   1800
ctggtgctga tggctatggt gaagcggaag gacttctgat aa                      1842
```

<210> SEQ ID NO 30
<211> LENGTH: 1815
<212> TYPE: DNA
<213> ORGANISM: Artificial Sequence
<220> FEATURE:
<223> OTHER INFORMATION: Synthetic Polynucleotide

<400> SEQUENCE: 30

```
atggcactga gcagcctgct gaaggtggtc accgccagcc tgtggctggg ccctggaatc     60
gcccagaaga tcacccagac ccagcccggc atgttcgtgc aggaaaaaga ggccgtcacc    120
ctggactgca cctacgacac cagcgacccc agctacggcc tgttctggta caagcagccc    180
agcagcggcg agatgatctt cctgatctac caggcagct acgaccagca gaacgccacc    240
gagggccggt acagcctgaa cttccagaag gcccggaagt ccgccaacct ggtcatcagc    300
gccagccagc tgggcgacag cgccatgtac ttttgcgcca tgaccagcgg cttcggcaac    360
gagaagctga ccttcggcac cggcacccgg ctgaccatca tccccaacga catccagaac    420
```

| | |
|---|---|
| cccgagcccg ccgtgtacca gctgaaggac cccagaagcc aggacagcac cctgtgcctg | 480 |
| ttcaccgact cgacagcca gatcaacgtg cccaagacaa tggaaagcgg caccttcatc | 540 |
| accgacaaga ccgtgctgga catgaaggct atggacagca agagcaacgg cgccattgcc | 600 |
| tggtccaacc agaccagctt cacatgccag gacatcttca agagacaaa cgccacctac | 660 |
| ccctccagcg acgtgccctg tgacgccacc ctgaccgaga agtccttcga cagacatg | 720 |
| aacctcaact tccagaacct gagcgtgatg ggcctgcgga tcctgctgct gaaagtggcc | 780 |
| ggcttcaacc tgctgatgac cctgcggctg tggtccagcc gggccaagag atctggcagc | 840 |
| ggcgccacca acttcagtct gctgaagcag gccggcgacg tggaagagaa ccctggccct | 900 |
| atgggcccag gcctgctgca ttggatggcc ctgtgtctgc tgggcaccgg acacggcgac | 960 |
| gctatggtca tccagaatcc cagataccag gtcacacagt tcggcaagcc cgtgaccctg | 1020 |
| agctgcagcc agaccctgaa ccacaacgtg atgtactggt atcagcagaa gtccagccag | 1080 |
| gccccccaagc tgctgttcca ctactacgac aaggacttca caacgaggc cgacaccccc | 1140 |
| gacaacttcc agagcagacg gcccaatacc agcttctgct cctggacat caggagcccc | 1200 |
| gggctgggcg acgctgctat gtacctgtgt gccaccagca gaggccaggg aggacagcct | 1260 |
| cagcactttg gcgacggcac cagactgagc atcctggaag atctgcggaa cgtgaccccc | 1320 |
| cccaaggtgt ccctgttcga gcccagcaag gccgagatcg ccaacaagca gaaagccacc | 1380 |
| ctcgtgtgcc tggccagagg cttcttcccc gaccacgtgg aactgtcttg gtgggtcaac | 1440 |
| ggcaaagagg tgcacagcgg cgtcagcacc gaccctcagg cctacaaaga gagcaactac | 1500 |
| agctactgcc tgagcagtcg gctgcgggtg tccgccacct tctggcacaa ccccggaac | 1560 |
| cacttcagat gccaggtgca gttccacggc ctgagcgaag aggacaagtg gcccgagggc | 1620 |
| agccccaagc tgtcaccca gaacatcagc gccgaggcct ggggcagagc ctgtggcatc | 1680 |
| accagcagct accagcaggg cgtgctgagc gccaccatcc tgtacgagat cctgctgggc | 1740 |
| aaggccaccc tgtacgccgt gctggtgtcc accctggtgg tcatggctat ggtcaagcgg | 1800 |
| aagaacagct gataa | 1815 |

```
<210> SEQ ID NO 31
<211> LENGTH: 672
<212> TYPE: DNA
<213> ORGANISM: Homo Sapiens

<400> SEQUENCE: 31
```

| | |
|---|---|
| atgaacggag acgacgcctt tgcaaggaga cccacggttg gtgctcaaat accagagaag | 60 |
| atccaaaagg ccttcgatga tattgccaaa tacttctcta aggaagagtg ggaaaagatg | 120 |
| aaagcctcgg agaaaatctt ctatgtgtat atgaagagaa agtatgaggc tatgactaaa | 180 |
| ctaggtttca aggccaccct cccaccttc atgtgtaata acgggccga agacttccag | 240 |
| gggaatgatt tggataatga ccctaaccgt gggaatcagg ttgaacgtcc tcagatgact | 300 |
| ttcggcaggc tccagggaat ctccccgaag atcatgccca gaagccagc agaggaagga | 360 |
| aatgattcgg aggaagtgcc agaagcatct ggcccacaaa atgatgggaa agagctgtgc | 420 |
| cccccgggaa aaccaactac ctctgagaag attcacgaga gatctggaaa tagggaggcc | 480 |
| caagaaaagg aagagagacg cggaacagct catcggtgga gcagtcagaa cacacacaac | 540 |
| attggtcgat tcagtttgtc aacttctatg ggtgcagttc atggtacccc caaaacaatt | 600 |
| acacacaaca gggaccaaa aggggggaac atgcctggac ccacagactg cgtgagagaa | 660 |
| aacagctggt ga | 672 |

<210> SEQ ID NO 32
<211> LENGTH: 9
<212> TYPE: PRT
<213> ORGANISM: Homo sapiens

<400> SEQUENCE: 32

Lys Tyr Ser Glu Lys Ile Ser Tyr Val
1               5

<210> SEQ ID NO 33
<211> LENGTH: 9
<212> TYPE: PRT
<213> ORGANISM: Homo sapiens

<400> SEQUENCE: 33

Lys Phe Ser Glu Lys Ile Ser Cys Val
1               5

<210> SEQ ID NO 34
<211> LENGTH: 9
<212> TYPE: PRT
<213> ORGANISM: Homo sapiens

<400> SEQUENCE: 34

Lys Ser Leu Glu Lys Ile Ser Tyr Val
1               5

<210> SEQ ID NO 35
<211> LENGTH: 91
<212> TYPE: PRT
<213> ORGANISM: Homo sapiens

<400> SEQUENCE: 35

Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Pro Ser Tyr
                20                  25                  30

Gly Leu Phe Trp Tyr Lys Gln Pro Ser Ser Gly Glu Met Ile Phe Leu
            35                  40                  45

Ile Tyr Gln Gly Ser Tyr Asp Gln Gln Asn Ala Thr Glu Gly Arg Tyr
        50                  55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe
                85                  90

<210> SEQ ID NO 36
<211> LENGTH: 90
<212> TYPE: PRT
<213> ORGANISM: Homo sapiens

<400> SEQUENCE: 36

Asp Ala Met Val Ile Gln Asn Pro Arg Tyr Gln Val Thr Gln Phe Gly
1               5                   10                  15

Lys Pro Val Thr Leu Ser Cys Ser Gln Thr Leu Asn His Asn Val Met
                20                  25                  30

Tyr Trp Tyr Gln Gln Lys Ser Ser Gln Ala Pro Lys Leu Leu Phe His
            35                  40                  45

Tyr Tyr Asp Lys Asp Phe Asn Asn Glu Ala Asp Thr Pro Asp Asn Phe
        50                  55                  60

```
Gln Ser Arg Arg Pro Asn Thr Ser Phe Cys Phe Leu Asp Ile Arg Ser
 65                  70                  75                  80

Pro Gly Leu Gly Asp Ala Ala Met Tyr Leu
                 85                  90

<210> SEQ ID NO 37
<211> LENGTH: 27
<212> TYPE: PRT
<213> ORGANISM: Artificial Sequence
<220> FEATURE:
<223> OTHER INFORMATION: Synthetic

<400> SEQUENCE: 37

Arg Ala Lys Arg Ser Gly Ser Gly Ala Thr Asn Phe Ser Leu Leu Lys
  1               5                  10                  15

Gln Ala Gly Asp Val Glu Glu Asn Pro Gly Pro
                 20                  25

<210> SEQ ID NO 38
<211> LENGTH: 81
<212> TYPE: DNA
<213> ORGANISM: Artificial Sequence
<220> FEATURE:
<223> OTHER INFORMATION: Synthetic

<400> SEQUENCE: 38
cgggccaagc ggtccggatc cggagccacc aacttcagcc tgctgaagca ggcgggcgac      60
gtggaggaga accccggccc c                                               81
```